(12) United States Patent
Kiani et al.

(10) Patent No.: US 9,375,570 B2
(45) Date of Patent: Jun. 28, 2016

(54) SENSOR UNIT FOR A FUNCTIONAL ELECTRICAL STIMULATION (FES) ORTHOTIC SYSTEM

(71) Applicant: Ensilver Canada, Markham (CA)

(72) Inventors: Farsad Kiani, Richmond Hill (CA); Qiang Song, Markham (CA); Jinbiao Zheng, Scarborough (CA)

(73) Assignee: Ensilver Canada, Markham (CA)

( * ) Notice: Subject to any disclaimer, the term of this patent is extended or adjusted under 35 U.S.C. 154(b) by 0 days.

(21) Appl. No.: 14/505,986

(22) Filed: Oct. 3, 2014

(65) Prior Publication Data

US 2015/0100105 A1 Apr. 9, 2015

Related U.S. Application Data

(60) Provisional application No. 61/886,173, filed on Oct. 3, 2013.

(51) Int. Cl.
*A61N 1/36* (2006.01)
*A43B 7/00* (2006.01)
*A61B 5/00* (2006.01)
(Continued)

(52) U.S. Cl.
CPC .......... *A61N 1/36003* (2013.01); *A61B 5/0002* (2013.01); *A61B 5/1038* (2013.01); *A61B 5/112* (2013.01); *A61B 5/1121* (2013.01); *A61B 5/6807* (2013.01); *A61B 5/6898* (2013.01); *A43B 3/0015* (2013.01); *A43B 7/00* (2013.01); *A43B 7/20* (2013.01)

(58) Field of Classification Search
USPC ................................ 600/587; 607/49; 36/140
See application file for complete search history.

(56) References Cited

U.S. PATENT DOCUMENTS 5,014,705 A 5/1991 Graupe et al.
5,016,635 A 5/1991 Graupe
(Continued)

FOREIGN PATENT DOCUMENTS

CA 2074532 A1 5/1992
CA 2794533 A1 5/2007
(Continued)

OTHER PUBLICATIONS

Bioness Inc., "Bioness LiveOn NESS H200 Wireless: User's Guide", 2011.

(Continued)

*Primary Examiner* — Carl H Layno
*Assistant Examiner* — Jon Eric C Morales
(74) *Attorney, Agent, or Firm* — Bereskin & Parr LLP/S.E.N.C.R.L., s.r.l.

(57) ABSTRACT

Various embodiments are described herein for a method and system for improving a gait of a user with a functional electrical stimulation (FES) orthotic system. In some described embodiments, the method includes receiving motion information associated with the gait of the user; generating a foot orientation indicator for the foot based on a foot acceleration and a foot angular velocity provided in the motion information; determining a foot condition based on at least the foot orientation indicator and the foot acceleration; and adjusting signal parameters for a stimulation signal based on at least the foot condition. The foot condition can indicate a gait quality of the user and therefore, the stimulation signal is applied to the user to adjust an orientation of the foot when the gait quality of the user requires improvement.

28 Claims, 15 Drawing Sheets

(51) Int. Cl.
*A61B 5/103* (2006.01)
*A61B 5/11* (2006.01)
*A43B 7/20* (2006.01)
*A43B 3/00* (2006.01)

(56) References Cited

U.S. PATENT DOCUMENTS

| | | |
|---|---|---|
| 5,070,873 A | 12/1991 | Graupe et al. |
| 5,092,329 A | 3/1992 | Graupe et al. |
| 6,324,432 B1 | 11/2001 | Rigaux et al. |
| 6,456,884 B1 | 9/2002 | Kenney |
| 7,147,667 B2 | 12/2006 | Bedard |
| 7,632,239 B2 | 12/2009 | Dar et al. |
| 7,660,636 B2 | 2/2010 | Castel et al. |
| 7,867,284 B2 | 1/2011 | Bedard |
| 7,899,556 B2 | 3/2011 | Nathan et al. |
| 7,949,403 B2 | 5/2011 | Palermo et al. |
| 8,057,486 B2 | 11/2011 | Hansen |
| 8,082,035 B2 | 12/2011 | Glukhovsky |
| D658,769 S | 5/2012 | Moser et al. |
| 8,167,640 B2 | 5/2012 | Ochoa et al. |
| 8,175,713 B1 | 5/2012 | Cywinski |
| 8,209,022 B2 | 6/2012 | Dar et al. |
| 8,209,036 B2 | 6/2012 | Nathan et al. |
| 8,332,029 B2 | 12/2012 | Glukhovsky et al. |
| 8,364,277 B2 | 1/2013 | Glukhovsky |
| 8,382,688 B2 | 2/2013 | Dar et al. |
| 8,463,390 B2 | 6/2013 | Muraoka |
| 2003/0125781 A1 | 7/2003 | Dohno et al. |
| 2003/0195586 A1 | 10/2003 | Rigaux et al. |
| 2003/0195587 A1 | 10/2003 | Rigaux et al. |
| 2004/0122483 A1 | 6/2004 | Nathan et al. |
| 2005/0261609 A1 | 11/2005 | Collings et al. |
| 2009/0030344 A1* | 1/2009 | Moser et al. .......... 600/587 |
| 2009/0240313 A1 | 9/2009 | Buhlmann |
| 2010/0042180 A1 | 2/2010 | Mueller et al. |
| 2010/0191316 A1 | 7/2010 | Buhlmann et al. |
| 2011/0093035 A1 | 4/2011 | Moser et al. |
| 2011/0125290 A1 | 5/2011 | Langlois |
| 2011/0137429 A1 | 6/2011 | Bedard |
| 2011/0152968 A1 | 6/2011 | Nathan et al. |
| 2011/0282412 A1 | 11/2011 | Glukhovsky et al. |
| 2012/0059298 A1 | 3/2012 | Hoffman et al. |
| 2012/0116478 A1 | 5/2012 | Buhlmann et al. |
| 2012/0203156 A1 | 8/2012 | Dar et al. |
| 2012/0330375 A1 | 12/2012 | Nathan et al. |
| 2012/0330394 A1 | 12/2012 | Dar et al. |
| 2012/0330395 A1 | 12/2012 | Dar et al. |
| 2013/0013041 A1 | 1/2013 | Glukhovsky et al. |
| 2014/0259799 A1* | 9/2014 | McDonnell et al. .......... 36/140 |
| 2015/0100104 A1* | 4/2015 | Kiani et al. .......... 607/49 |
| 2015/0100107 A1 | 4/2015 | Kiani et al. |

FOREIGN PATENT DOCUMENTS

| | | |
|---|---|---|
| CA | 2649663 A1 | 11/2007 |
| CA | 2663030 A1 | 4/2008 |
| CA | 2697381 A1 | 2/2009 |
| CA | 2727812 A1 | 12/2009 |
| CA | 2732751 A1 | 2/2010 |
| CA | 2780328 A1 | 6/2011 |
| CA | 2782677 A1 | 6/2011 |
| CN | 202078650 U | 12/2011 |
| DE | 60 2004 005 692 T2 | 12/2007 |
| EP | 1201266 A1 | 5/2002 |
| EP | 1435891 A4 | 4/2003 |
| EP | 1530493 A1 | 3/2004 |
| EP | 1819395 A2 | 6/2006 |
| EP | 1874398 A4 | 10/2006 |
| EP | 1874404 A2 | 10/2006 |
| EP | 2037804 A2 | 12/2007 |
| EP | 1095670 B1 | 5/2008 |
| EP | 2120801 A1 | 7/2008 |
| EP | 1531767 B1 | 10/2008 |
| EP | 1980224 A2 | 10/2008 |
| EP | 2152359 A2 | 12/2008 |
| EP | 2180918 A2 | 2/2009 |
| EP | 2194862 A1 | 3/2009 |
| EP | 2247249 A1 | 8/2009 |
| EP | 2252242 A1 | 8/2009 |
| EP | 2291220 A1 | 12/2009 |
| EP | 2320993 A1 | 2/2010 |
| EP | 2506918 A1 | 6/2011 |
| EP | 2506919 A1 | 6/2011 |
| EP | 2392381 A2 | 12/2011 |
| EP | 1531766 B1 | 1/2012 |
| EP | 2097851 B1 | 2/2012 |
| EP | 2012669 B1 | 3/2013 |
| EP | 2586489 A1 | 5/2013 |
| JP | 201275933 A | 4/2012 |
| KR | 10-2005-0042793 A | 5/2005 |
| KR | 10-2005-0058417 A | 6/2005 |
| KR | 10-2006-0100427 A | 9/2006 |
| KR | 10-2009-0025184 A | 3/2009 |
| WO | 9209328 A1 | 6/1992 |
| WO | 2005-122740 A3 | 12/2005 |
| WO | 2006-061804 A8 | 6/2006 |
| WO | 2006-113802 A2 | 10/2006 |
| WO | 2007-125534 A2 | 11/2007 |
| WO | 2008-043065 A2 | 4/2008 |
| WO | 2008-086629 A1 | 7/2008 |
| WO | 2009-021157 A1 | 2/2009 |
| WO | 2009-026588 A2 | 2/2009 |
| WO | 2009-038861 A1 | 3/2009 |
| WO | 2009-052134 A1 | 4/2009 |
| WO | 2009-052135 A1 | 4/2009 |
| WO | 2009-088563 A1 | 7/2009 |
| WO | 2009-137234 A2 | 11/2009 |
| WO | 2009-155436 A1 | 12/2009 |
| WO | 2009-158389 A1 | 12/2009 |
| WO | 2010-002517 A1 | 1/2010 |
| WO | 2010-017004 A1 | 2/2010 |
| WO | 2010-107648 A1 | 9/2010 |
| WO | 2011-068823 A1 | 6/2011 |
| WO | 2011-068849 A1 | 6/2011 |
| WO | 2013-001526 A2 | 6/2012 |
| WO | 2012-107921 A1 | 8/2012 |
| WO | 2012-150500 A1 | 11/2012 |

OTHER PUBLICATIONS

Bioness Inc., "Bioness LiveOn NESS L300Plus: User's Guide", 2011.
Bioness Inc., "Bioness LiveOn NESS L300: Clinician's Guide", 2010.
Innovative Neurotronics, "WalkAide System: User Manual", 2010.
Co-pending U.S. Appl. No. 14/529,854, filed Oct. 31, 2014, entitled "Cuff Unit Fora Functional Electrical Stimulation (FES) Orthotic System".

* cited by examiner

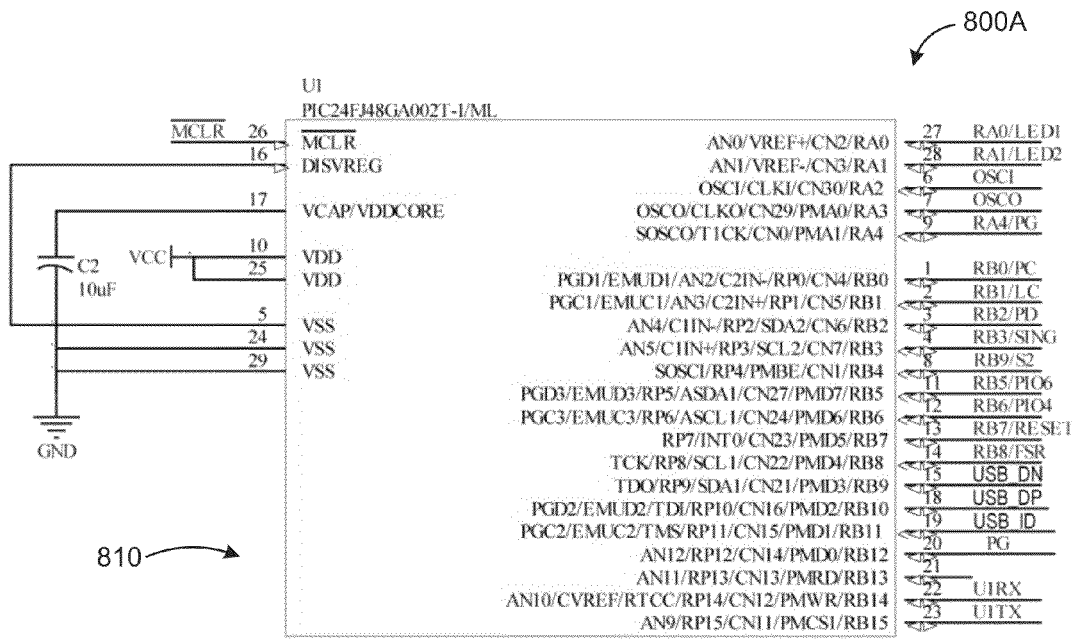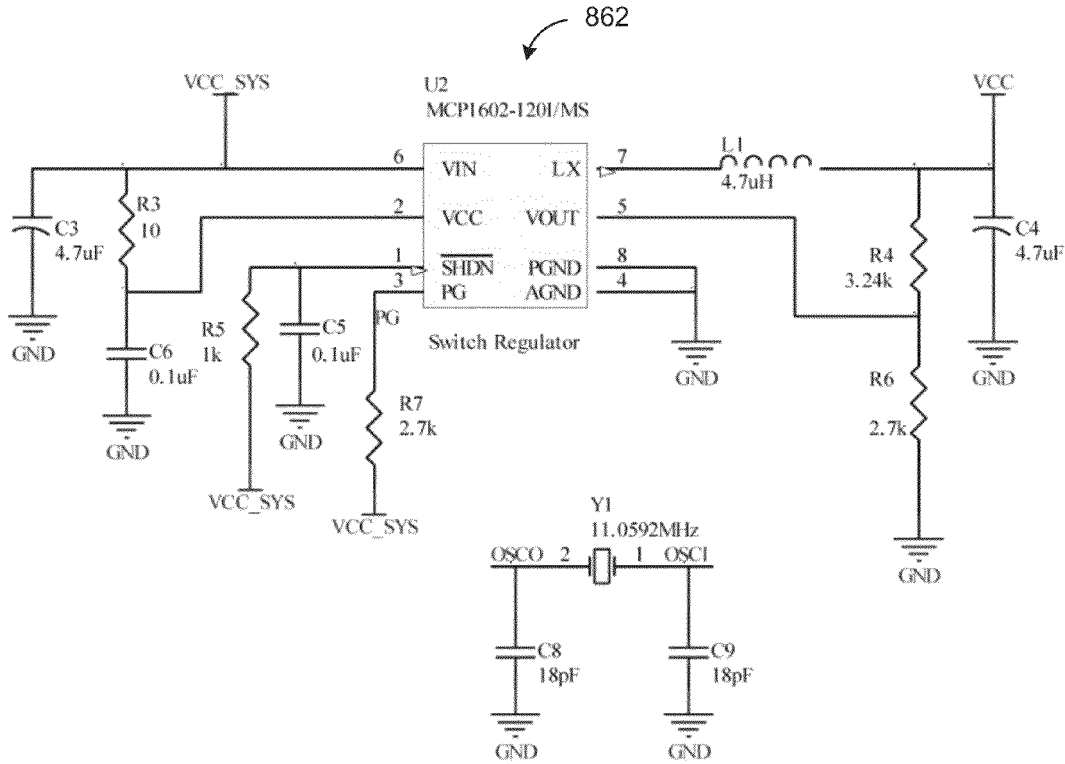
FIG. 8A

SENSOR UNIT FOR A FUNCTIONAL ELECTRICAL STIMULATION (FES) ORTHOTIC SYSTEM

CROSS REFERENCE TO RELATED APPLICATIONS

This application claims the benefit of U.S. Provisional Patent Application No. 61/886,173, filed Oct. 3, 2013 the entire contents of which are hereby incorporated by reference.

FIELD

The embodiments described herein relate to a sensor unit for a functional electrical stimulation (FES) orthotic system, and in particular, methods and systems for improving a gait of a user with the FES orthotic system.

BACKGROUND

Individuals suffering from a central nervous system injury, such as a stroke, a brain injury, multiple sclerosis, cerebral palsy or partial spinal cord injuries, or other medical conditions may have mobility problems due to that injury or medical condition. Functional electrical stimulation (FES) systems may assist those individuals address those mobility problems.

Existing FES systems provide electrical stimulation to muscles that may have been paralyzed or affected by the central nervous system injury or other medical conditions. The electrical stimulation may facilitate motion in those affected muscles. In some cases, FES systems may also help reeducate muscle movement, retard atrophy of any affected muscles due to disuse, and maintain or increase a range of motion at nearby joints.

An example application of an FES system is to enhance ankle dorsiflexion for individuals experiencing foot drop. Foot drop is a gait abnormality that stems from a weakness in a foot, damage to a peroneal nerve, or paralysis of muscles in an anterior portion of a lower leg. Foot drop may be caused by various conditions, such as muscle or spinal nerve trauma, abnormal anatomy, toxins and disease. Individuals affected by foot drop are unable to lift their foot and toes during a swing phase of their gait thereby causing their toes to be caught by the ground and their foot to drag on the ground. The FES system can assist those individuals by sending electrical stimulation signals to the affected muscles during the swing phase of their gait in order to trigger movement in those muscles so that the foot is lifted and not dragged along the ground.

Although existing FES systems are generally portable, they tend to be bulky and therefore, cumbersome for users to carry around on a daily basis. Existing FES systems also tend to lack versatility in operation and offer limited functionality.

SUMMARY

In a broad aspect, at least one embodiment described herein provides a method of improving a gait of a user with a functional electrical stimulation (FES) orthotic system. The method comprises receiving motion information associated with the gait of the user, the motion information comprising a foot acceleration and a foot angular velocity of the foot of the user; generating a foot orientation indicator for the foot based on the foot acceleration and the foot angular velocity, the foot orientation indicator corresponding to an angular position relative to a longitudinal axis of the foot; determining a foot condition based on at least the foot orientation indicator and the foot acceleration, the foot condition indicating a gait quality of the user; and adjusting signal parameters for a stimulation signal based on at least the foot condition, the stimulation signal being applied to the user to adjust an orientation of the foot when the gait quality of the user requires improvement.

In at least one embodiment, the foot orientation indicator may comprise one or more orientation indicators and each of the one or more orientation indicators corresponds to a different direction of the angular position.

In at least one embodiment, determining the foot condition may further comprise determining the foot condition is a normal condition when the one or more orientation indicators is less than an orientation threshold and the foot acceleration is less than an acceleration threshold; and determining the foot condition is an impaired condition when at least one of the orientation indicators is greater than or equal to the orientation threshold and the foot acceleration is greater than or equal to the acceleration threshold.

In at least one embodiment, the orientation threshold may be approximately 15 degrees.

In at least one embodiment, the orientation threshold may comprise a different orientation threshold for each of the different orientation indicators.

In at least one embodiment, the acceleration threshold may be approximately 1.9 g.

In at least one embodiment, generating the foot orientation indicator for the foot further may comprise compensating the foot angular velocity with the foot acceleration.

In at least one embodiment, the act of compensating may comprise applying Kalman filtering to the foot acceleration and the foot angular velocity.

In at least one embodiment, the method may further comprise pre-processing each of the foot angular velocity and the foot acceleration to remove extraneous data.

In at least one embodiment, the step of pre-processing may comprise applying a recurrence average filter for pre-processing.

In at least one embodiment, the method may further comprise receiving environmental data associated with a surrounding of the user; and adjusting the signal parameters for the stimulation signal based on the environmental data. Furthermore, in at least one embodiment, the environmental data may comprise a temperature of the surrounding environment of the user.

In at least one embodiment, the foot acceleration may be received from an accelerometer.

In at least one embodiment, the foot angular velocity may be received from a gyroscope.

In at least one embodiment, the motion information may further comprise an amount of force exerted by the foot of the user that is used to determine if the user is taking a step or shifting their weight, wherein if the user is shifting their weight, the stimulation signal is not adjusted.

In another broad aspect, at least one embodiment described herein provides a functional electrical stimulation (FES) orthotic system for improving a gait of a user. The FES orthotic system comprising a sensor unit comprising a sensor processor and a plurality of sensors, the sensor processor being configured to receive motion information associated with the gait of the user, the motion information comprising a foot acceleration and a foot angular velocity of the foot of the user; generate a foot orientation indicator for the foot based on the foot acceleration and the foot angular velocity, the foot orientation indicator corresponding to an angular position relative to a longitudinal axis of the foot; determine a foot condition based on at least the foot orientation indicator and the foot acceleration, the foot condition indicating a gait quality of the user; and adjust signal parameters for a stimulation signal based on at least the foot condition, the stimulation signal being applied to the user to adjust an orientation of the foot when the gait quality of the user requires improvement.

In at least one embodiment, the sensor processor may further be configured to determine the foot condition is a normal condition when the orientation indicators is less than an orientation threshold and the foot acceleration is less than an acceleration threshold; and determine the foot condition is an impaired condition when at least one of the orientation indicators is greater than or equal to the orientation threshold and the foot acceleration is greater than or equal to the acceleration threshold.

In at least one embodiment, the sensor processor may further be configured to compensate the foot angular velocity with the foot acceleration.

In at least one embodiment, the sensor processor may further be configured to apply a Kalman filter to the foot acceleration and the foot angular velocity.

In at least one embodiment, the sensor processor may further be configured to pre-process each of the foot angular velocity and the foot acceleration to remove extraneous data.

In at least one embodiment, the sensor processor may further be configured to apply a recurrence average filter for pre-processing.

In at least one embodiment, the sensor processor may further be configured to receive environmental data associated with a surrounding of the user; and adjust the signal parameters for the stimulation signal based on the environmental data. Furthermore, in at least one embodiment, the environmental data comprises a temperature of the surrounding environment of the user.

In at least one embodiment, the sensor unit may comprise an accelerometer to provide foot acceleration data.

In at least one embodiment, the sensor unit may comprise a gyroscope to provide foot angular velocity data.

In another broad aspect, at least one embodiment described herein provides a computer readable medium comprising a plurality of instructions executable on a processor of a device for adapting the processor to implement a method of improving a gait of a user with a functional electrical stimulation (FES) orthotic system. The method may comprise receiving motion information associated with the gait of the user, the motion information comprising a foot acceleration and a foot angular velocity of the foot of the user; generating a foot orientation indicator for the foot based on the foot acceleration and the foot angular velocity, the foot orientation indicator corresponding to an angular position relative to a longitudinal axis of the foot; determining a foot condition based on at least the foot orientation indicator and the foot acceleration, the foot condition indicating a gait quality of the user; and adjusting signal parameters for a stimulation signal based on at least the foot condition, the stimulation signal being applied to the user to adjust an orientation of the foot when the gait quality of the user requires improvement.

In at least one embodiment, the computer readable medium may comprise instructions for performing any of the methods described in accordance with the teachings herein.

Other features and advantages of the present application will become apparent from the following detailed description taken together with the accompanying drawings. It should be understood, however, that the detailed description and the specific examples, while indicating preferred embodiments of the application, are given by way of illustration only, since various changes and modifications within the spirit and scope of the application will become apparent to those skilled in the art from this detailed description.

DETAILED DESCRIPTION OF DRAWINGS

For a better understanding of the various embodiments described herein, and to show more clearly how these various embodiments may be carried into effect, reference will be made, by way of example, to the accompanying drawings which show at least one example embodiment, and in which:

FIGS. 8A, 8B and 8C illustrate a circuit design of the sensor unit in accordance with an example embodiment;

Figure 1:
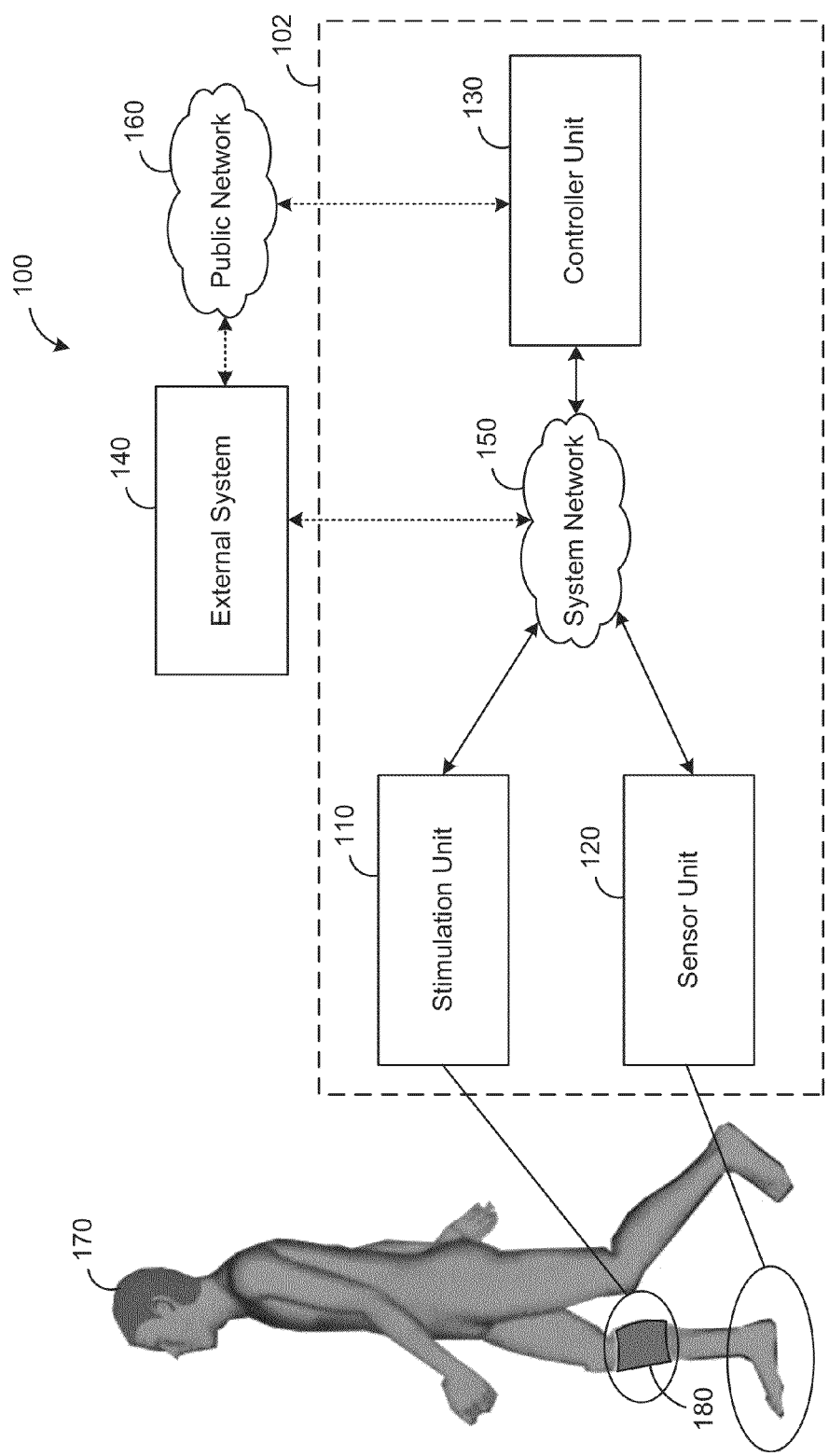
FIG. 1 is a block diagram of components interacting with a functional electrical stimulation (FES) system in accordance with an example embodiment.

Further aspects and advantages of the embodiments described herein will appear from the following description taken together with the accompanying drawing.

DESCRIPTION OF EXAMPLE EMBODIMENTS

The various embodiments described herein generally relate to methods, and associated systems configured to implement the methods, of improving a gait of a user with a functional electrical stimulation (FES) orthotic system. The gait is a manner in which the user is moving, such as how the user is walking or stepping.

The methods described herein involve receiving motion information that is associated with the gait of the user. The motion information can be used for determining a foot condition of the user. The foot condition may indicate a gait quality so that the FES orthotic system may define signal parameters for a stimulation signal that can improve the gait of that user, in particular when the gait quality of the user requires improvement. The FES orthotic system may define the signal parameters by adjusting signal parameters for the stimulation signal.

The motion information may include information associated with an acceleration of the foot and information associated with an angular velocity of the foot. The FES orthotic system can generate a foot orientation indicator based on the received motion information. The foot orientation indicator can represent an angular position of the foot relative to a longitudinal axis of the foot. For users with mobility issues, such as foot drop, the angular position of the foot may not be controllable, or easily controllable, by the user. When the angular position of the foot cannot be properly controlled by the user, the orientation of the foot can impair the gait of the user. By determining the foot orientation indicator, the FES orthotic system can identify a current foot condition and adjust signal parameters for a stimulation signal to adjust an orientation of the foot accordingly.

Various apparatuses or processes will be described below to provide an example of an embodiment of the claimed subject matter. No embodiment described below limits any claimed subject matter and any claimed subject matter may cover processes or apparatuses that differ from those described below. The claimed subject matter is not limited to apparatuses or processes having all of the features of any one apparatus or process described below or to features common to multiple or all of the apparatuses or processes described below. It is possible that an apparatus or process described below is not an embodiment of any claimed subject matter. Any subject matter that is disclosed in an apparatus or process described below that is not claimed in this document may be the subject matter of another protective instrument, for example, a continuing patent application, and the applicants, inventors or owners do not intend to abandon, disclaim or dedicate to the public any such claimed subject matter by its disclosure in this document.

Furthermore, it will be appreciated that for simplicity and clarity of illustration, where considered appropriate, reference numerals may be repeated among the figures to indicate corresponding or analogous elements. In addition, numerous specific details are set forth in order to provide a thorough understanding of the example embodiments described herein. However, it will be understood by those of ordinary skill in the art that the example embodiments described herein may be practiced without these specific details. In other instances, well-known methods, procedures and components have not been described in detail so as not to obscure the example embodiments described herein. Also, the description is not to be considered as limiting the scope of the example embodiments described herein.

It should also be noted that the terms "coupled" or "coupling" as used herein can have several different meanings depending in the context in which these terms are used. For example, the terms coupled or coupling can have a mechanical or electrical connotation. For example, as used herein, the terms coupled or coupling can indicate that two elements or devices can be directly connected to one another or connected to one another through one or more intermediate elements or devices via an electrical element, electrical signal or a mechanical element depending on the particular context.

It should be noted that terms of degree such as "substantially", "about" and "approximately" as used herein mean a reasonable amount of deviation of the modified term such that the end result is not significantly changed. These terms of degree may also be construed as including a deviation of the modified term if this deviation would not negate the meaning of the term it modifies.

Furthermore, the recitation of numerical ranges by endpoints herein includes all numbers and fractions subsumed within that range (e.g. 1 to 5 includes 1, 1.5, 2, 2.75, 3, 3.90, 4, and 5). It is also to be understood that all numbers and fractions thereof are presumed to be modified by the term "about" which means a variation of up to a certain amount of the number to which reference is being made if the end result is not significantly changed.

The embodiments of the systems and methods described herein may be implemented using a combination of hardware and software. These embodiments may be implemented in part using computer programs executing on programmable devices, each programmable device including at least one processor, a data storage system (including volatile memory or non-volatile memory or other data storage elements or a combination thereof), and at least one communication interface. For example, and without limitation, the programmable devices (referred to herein as computing devices) may be a server, network appliance, an embedded device, a computer expansion module, a personal computer, a laptop, a personal data assistant, a cellular telephone, a smart-phone device, a tablet computer, a wireless device or any other computing device capable of being configured to carry out the methods described herein. The particular embodiment depends on the application of the computing device. For example, a server can be used to provide a centralized database and/or a remote programming interface while an embedded device may be used for components that are worn or otherwise directly used by the user.

In some embodiments, the communication interface may be a network communication interface. In embodiments in which elements are combined, the communication interface may be a software communication interface, such as those for inter-process communication (IPC). In still other embodiments, there may be a combination of communication interfaces implemented as hardware, software, and a combination thereof.

Program code may be applied to input data to perform at least some of the functions described herein and to generate output information. The output information may be applied to one or more output devices, in known fashion.

At least some of the programs may be implemented in a high level procedural or object oriented programming and/or scripting language, or both, to communicate with a computer system. However, other programs may be implemented in assembly or machine language, if desired. In any case, the language may be a compiled or interpreted language. The computer programs may be stored on a storage media or a device (e.g. ROM, magnetic disk, optical disc) readable by a general or special purpose programmable device, for configuring and operating the programmable device when the storage media or device is read by the programmable device to perform the procedures described herein. Embodiments of the system may also be considered to be implemented as a non-transitory computer-readable storage medium, configured with a computer program, where the storage medium so configured causes a computing device to operate in a specific and predefined manner to perform the functions described herein.

Furthermore, some of the programs associated with the system, processes and methods of the embodiments described herein are capable of being distributed in a computer program product comprising a computer readable medium that bears computer usable instructions for one or more processors. The medium may be provided in various forms, including non-transitory forms such as, but not limited to, one or more diskettes, compact disks, tapes, chips, and magnetic and electronic storage. In alternative embodiments the medium may be transitory in nature such as, but not limited to, wireline transmissions, satellite transmissions, internet transmissions (e.g. downloads), media, digital and analog signals, and the like. The computer useable instructions may also be in various formats, including compiled and non-compiled code.

Reference is first made to FIG. 1, which shows a block diagram 100 of components interacting with a functional electrical stimulation (FES) system 102 in accordance with an example embodiment. The FES system 102 generates stimulation signals to assist individuals, such as a user 170 of FIG. 1, with weakened, impaired or paralyzed muscles in a lower leg. The FES system 102 may generate stimulation signals for various purposes, such as to facilitate movement of the user 170, to reeducate any affected muscles in the user 170, to retrain the user 170 to walk, or to retard atrophy in muscles due to disuse, for example.

When facilitating movement of the user 170, the FES system 102 can generate stimulation signals to trigger movement at affected muscles. In the case of a user 170 with foot drop, for example, the FES system 102 may generate stimulation signals that are synchronized with a swing phase of a gait of that user 170 in order to help that user 170 lift the foot and prevent the foot from dragging on the ground.

As shown in FIG. 1, the FES system 102 includes a stimulation unit 110, a sensor unit 120 and a controller unit 130. The operation of the stimulation unit 110, the sensor unit 120 and the controller unit 130 will now be further described.

The stimulation unit 110, the sensor unit 120 and the controller unit 130 may communicate with each other via system network 150. As also shown in FIG. 1, the FES system 102 may also communicate with an external system 140 via the system network 150 and/or possibly via a public network 160. As will be described, the FES system 102 may receive signal parameters and other operational instructions from the external system 140 and may also transmit operational data to the external system 140.

Each of the stimulation unit 110, the sensor unit 120 and the controller unit 130 may include a real time calendar and clock (RTCC) component. The RTCC component may require a low frequency crystal or oscillator in order to operate. The RTCC component provides real time date and time information for the FES system 102. The date information may include the year, month, day and week, and the time information may include the hour, minute, and second. The RTCC component may continue to operate even when the FES system 102 is in a sleep mode. Therefore, the RTCC component can facilitate system operations in which accurate time information is needed and with minimal power consumption. For example, the RTCC component can help ensure that a timer module at each of the stimulation unit 110, the sensor unit 120 and the controller unit 130 is synchronized so that stimulation signals are triggered at the appropriate time.

The FES system 102 may also enter into a safe mode in response to any communication errors between any two of the stimulation unit 110, the sensor unit 120 and the controller unit 130, as well as between the FES system 102 and the external system 140. For example, when the system network 150 fails to operate properly, the stimulation unit 110 may enter the safe mode and generate a predetermined safe stimulation signal for the user 170, no stimulation signal or provide a warning to the user 170 that a component of the FES system 102 is not functioning properly.

The stimulation unit 110 generates and delivers electrical stimulation signals to the user 170. As shown in FIG. 1, the stimulation unit 110 may be provided in association with a cuff 180 that is worn by the user 170 at a location on the user that is to receive the stimulation signals. In the example of FIG. 1, the cuff 180 is worn on the lower leg of the user 170 to stimulate nerves located in the lower leg. The stimulation unit 110 may include various modules for generating and delivering the stimulation signal to the user 170. It will be understood that the various modules may be hardware, software, and a combination of hardware and software. The stimulation unit 110 may be implemented in several ways as is known by those skilled in the art.

The stimulation unit 110 may generate stimulation signals based on signal parameters stored at the stimulation unit 110 or signal parameters received via the system network 150 from the external system 140 or the controller unit 130. The signal parameters received from the controller unit 130 may be determined based on a variety of factors, including an operational mode of the FES system 102 as selected by the user 170, data provided from waveform data charts and waveform parameters, and stimulation parameters as selected by the user 170 and a third party, such as a doctor or clinician. The signal parameters received from the external system 140 may include stimulation parameters as selected by the third party. In some embodiments, the stimulation unit 110 may vary amplitude or frequency of a stimulation signal based on the signal parameters.

In some embodiments, the stimulation unit 110 may generate multiple stimulation signals to different nerves of the user 170. By stimulating different nerves, different functionalities may be achieved by the FES system 102. The different stimulation signals may be generated at approximately the same time. For example, one to eight stimulation channels may be available at the stimulation unit 110 for generating up to eight stimulation signals. Each stimulation channel may be used for stimulating a different nerve, for example.

To deliver the stimulation signal, the stimulation unit 110 includes at least one electrode that is positioned substantially around a target muscle or a target nerve that is to receive the stimulation signal.

The stimulation unit 110 may also generate operation data, such as stimulation status data, to be displayed at the cuff 180 or by the controller unit 130. For example, the stimulation unit 110 may include a display component, such as an LCD display in some cases.

The sensor unit 120 includes multiple different sensors for detecting data associated with a gait of the user 170 or an environment of the user 170. As shown in FIG. 1, similar to the stimulation unit 110, the sensor unit 120 is generally worn by the user 170. In the example of FIG. 1, the sensor unit 120 is located at the foot of user 170. The sensor unit 120 may be attached to footwear worn by the user 170 or embedded into or otherwise attached to an insole of the user's footwear.

The sensor unit 120 may process at least a portion of the detected sensor data to generate various signal parameters for the stimulation signal. The sensor unit 120 may also transmit the detected sensor data to other components of the FES system 102, such as stimulation unit 110 and controller unit 130, and the external system 140. The detected sensor data may be transmitted in various data formats, such as in a hexadecimal byte format.

Various sensors may be provided at the sensor unit 120. The sensors may include a force sensor, a temperature sensor, a gyroscope, an accelerometer, and a compass. Different embodiments may include all or different combinations of the aforementioned sensors.

The force sensor can detect an amount of force that it receives. For a sensor unit 120 that is located near or in the insole of the footwear of the user 170, the force sensor can detect the amount of force that is exerted by the foot of the user 170 while the user 170 walks. Based on data collected by the force sensor, the FES system 102 may distinguish between various movements of the user 170, such as whether that user 170 is standing, shifting their weight, is in mid-stride or is performing other activities.

The temperature sensor can detect a temperature of an environment of the user 170, for example.

The gyroscope can detect an angular velocity of the sensor unit 120 when the sensor unit 120 is in motion. Based on the detected angular velocity, the FES system 102 may determine an orientation of the sensor unit 120 and therefore an orientation of the foot of the user 170.

The accelerometer can detect an acceleration of the sensor unit 120.

The compass can detect a geomagnetic field of the sensor unit 120 to determine the direction in which the user 170 is walking.

The sensor unit 120 may also track a passage of time with a timer module, and transmit the time data via the system network 150. The sensor unit 120 may track the passage of time to facilitate data collection. For example, the sensor unit 120 may collect sensor data at predetermined time intervals, such as every 10 milliseconds, for example. A timer module may help to trigger data collection at the sensor unit 120. When the FES system 102 is used for addressing foot drop, the sensor unit 120 may track the passage of time to generate a lift period of the foot. The lift period is a period of time from when the user 170 lifts the foot from the ground to when that foot returns to the ground. The lift period may be used for generating the signal parameters for the stimulation signal.

The controller unit 130 can define the signal parameters of the stimulation signal and transmit the signal parameters to the stimulation unit 110 via the system network 150. The controller unit 130 may define the signal parameters based on data received from the sensor unit 120, the external system 140, or parameters stored locally or received at the controller unit 130.

The controller unit 130 is generally carried or worn by the user 170. The controller unit 130 may be a controller device dedicated for use with the FES system 102. The controller unit 130 may be attached to a waist of user 170, for example. The controller device includes hardware and software modules for operating and interacting with each of the other units in the FES system 102 as well as external system 140. The controller unit 130 may also be provided as a controller software module that is installed onto existing computing devices that are carried by the user 170. The computing devices may include, but is not limited to, an electronic tablet device, a personal computer, a portable computer, a mobile device, a personal digital assistant, a laptop, a smart phone, a WAP phone, a handheld interactive television, handheld video display terminals, gaming consoles, and other portable electronic devices, for example. The controller software module may include one or more software modules for operating and interacting with each of the other units in the FES system 102 as well as external system 140.

Figure 2:
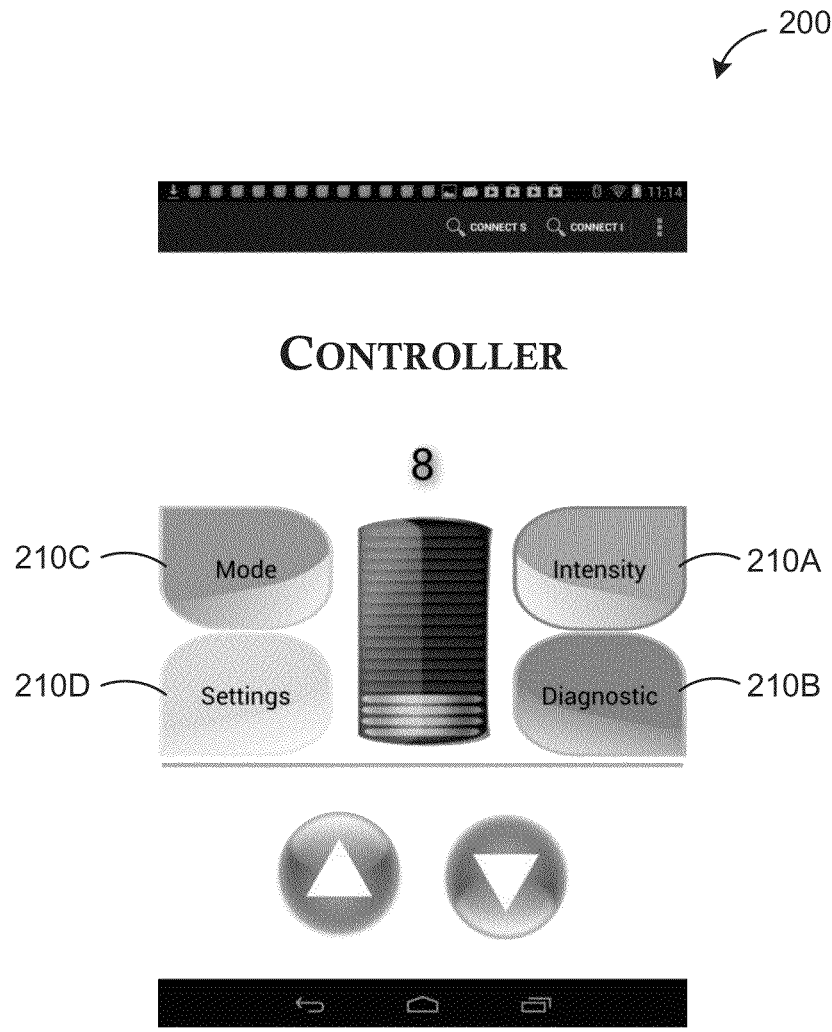
FIG. 2 illustrates an example embodiment of a user interface for a controller unit of the FES system.

In at least some embodiments, the controller unit 130 provides a user control interface from which to receive user inputs for operating the FES system 102. An example user control interface 200 for controller unit 130 is illustrated in FIG. 2. The user control interface 200 includes more icons 210, such as an intensity icon 210A, a diagnostic icon 210B, a mode icon 210C and a settings icon 210D, with which user 170 can use for interacting with the FES system 102. It will be understood that the user control interface 200 may include more or fewer icons than shown in FIG. 2, and that the icons may be different from those shown in FIG. 2.

When the controller unit 130 receives a user input activating the intensity icon 210A, the controller unit 130 may allow the user 170 to vary an intensity level of the stimulation signal. Similarly, when the controller unit 130 receives a user input activating the settings icon 210D, the controller unit 130 may allow the user 170 to alter certain operational conditions of the FES system 102. The operational conditions that may be altered may vary based on user type. For example, the user 170 may be limited to cosmetic changes to the user control interface 200, such as background colour, but a doctor or clinician with access to the user control interface 200 may have increased access, such as to alter signal parameters.

In response to receiving a user input activating the mode icon 210C, the controller unit 130 may enable the user 170 to change the operational mode of the FES system 102. Depending on the mode selected by the user 170, the controller unit 130 may vary the signal parameters accordingly.

As described, the FES system 102 may be used for different purposes, such as to facilitate movement of user 170, to reeducate any affected muscles, to retrain the user 170 to walk, or to retard atrophy of muscles due to disuse. Therefore, the FES system 102 may operate in different modes, such as a training mode, a walking mode, a test mode, and a sleep mode. The various different modes may be associated with stimulation signals having different intensity levels and frequencies. It will be understood that fewer or additional number of operational modes may be provided by the controller unit 130 in different embodiments.

The training mode may be used for reeducating affected muscles or to retard atrophy of muscles while the user 170 is sitting or lying down. The training mode may therefore be associated with stimulation signals that are not dependent on a movement of the user 170. Instead, the stimulation signals applied to the user 170 during the training mode can have a variety of intensities and frequencies. The training mode may also be used for initially fitting the user 170 with the stimulation unit 110.

The walking mode may be used for facilitating movement of the user 170. As a result, the walking mode may be associated with stimulation signals that are dependent on the movement of the user 170, unlike the stimulation signals associated with the training mode.

The test mode may be used for conducting functional tests and diagnostics of the FES system 102 in order to identify causes of any errors in the FES system 102. The test mode may also be used during calibration or repair of the FES system 102. For example, when the FES system 102 is in the test mode, the stimulation unit 110 may generate predefined stimulation signals at specific frequencies that can be identified for facilitating calibration.

The sleep mode can help the FES system 102 conserve power. Although each of the stimulation unit 110, the sensor unit 120 and the controller unit 130 may be equipped with a power supply, such as rechargeable lithium-ion batteries, power saving can be important for extending a battery life of the FES system 102. Various different power states, such as a power down state, a low power state and an energy saving state may be used. For example, when the sleep mode is selected, the controller unit 130 may power down at least one of the stimulation unit 110 and the sensor unit 120, or place one of the stimulation unit 110 and the sensor unit 120 in a low power state or energy saving state.

In another example of when the sleep mode is selected, the controller unit 130 may synchronize a power usage state as between each of the stimulation unit 110, the sensor unit 120 and the controller unit 130. For synchronizing a low power state among the stimulation unit 110, the sensor unit 120 and the controller unit 130, the controller unit 130 may first transmit a low power state signal to the stimulation unit 110 via the system network 150. Once the stimulation unit 110 enters the low power state, the stimulation unit 110 may send a low power state signal to the sensor unit 120. After the sensor unit 120 enters the low power state, the sensor unit 120 may send a low power state signal to the controller unit 130. In response to receiving the low power state signal, the controller unit 130 transitions to a low power state. The power consumption of the FES system 102 during a low power state can be a nominal amount.

Each of the stimulation unit 110, the sensor unit 120 and the controller unit 130 can exit the sleep mode in response to receipt of an interrupt signal. The interrupt signal may be a user input received by the controller unit 130 for changing the operation mode from sleep mode, a physical movement of the user 170 as detected by the sensor unit 120, such as detection of a pressure change by the force sensor, or a user input received by the stimulation unit 110.

Still referring to FIG. 2, when the controller unit 130 receives a user input indicating that the diagnostic icon 210B is selected, the controller unit 130 may prepare reports based on data associated with the operation of the FES system 102. The data associated with the operation of the FES system 102 may be stored with at least one of the controller unit 130 and remotely at external system 140.

The reports may be statistical reports or various usage reports. The operation data may include any data received from the sensor unit 120 and external system 140, and any data collected by the controller unit 130, such as error logs, usage logs, previous waveform parameters, and current waveform parameters. The usage logs may include time and date data, length of use, distance covered, speed, location data (e.g., data provided from the Global Positioning System (GPS)) and other related data.

Figure 3B:
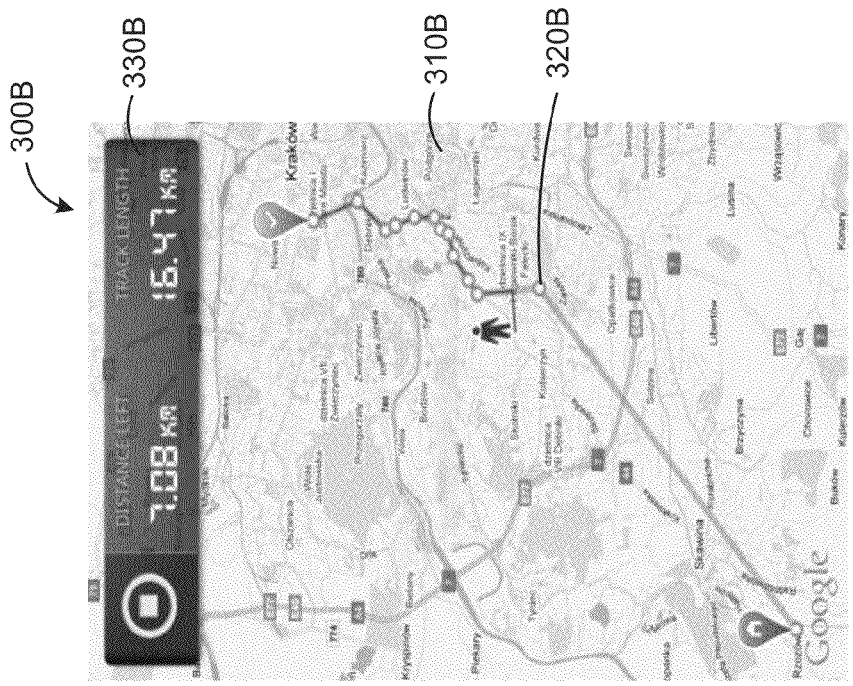
FIGS. 3A and 3B are example screenshots of usage reports generated by the controller unit of the FES system.
Figure 3A:
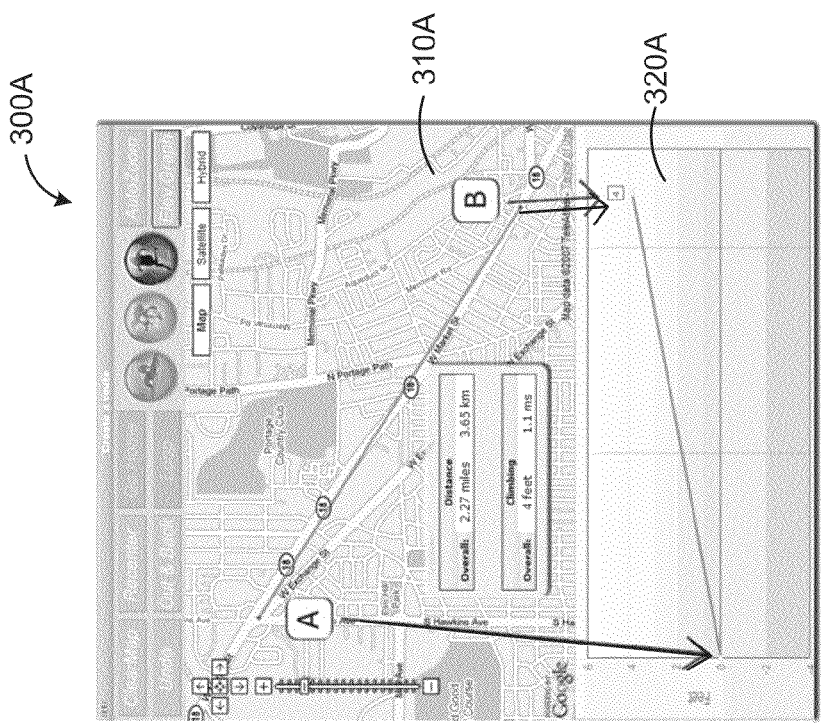

Reference is now made to FIGS. 3A and 3B, which are example usage reports 300A and 300B, respectively, generated by the controller unit 130.

The usage report 300A illustrates a workout performance report. The controller unit 130 may generate a map 310A illustrating a route covered by the user 170 during the workout as well as a progress display 320A illustrating a progress of the user 170. The controller unit 130 may additionally provide other performance evaluations, such as the amount of calories burned during the workout. Similarly, the usage report 300B is also a workout performance report. The usage report 300B includes a map 310B of the route of the user 170, a progress display 320B illustrating the progress of the user 170, and a usage summary 330B. For example, the progress display 320B can represent a speed of the user 170 by varying segments of the route based on the speed of the user 170 during that segment. If the user 170 is moving at a first speed during a first segment of the route, that first segment can be shown in the progress display 320B in a first colour or with a first pattern (e.g., solid line). If the user 170 then moves at a second speed that is different from the first speed during a second segment of the route, that second segment can be shown in the progress display 320B in a second colour that is different from the first colour or second pattern that is different from the first pattern (e.g., dotted line). Other manners of varying the display of the segments of the route may be used.

The reports generated by the controller unit 130 may be transmitted to the external system 140. Doctors, clinicians or other medical professionals who receive the reports via the external system 140 may review the reports and adjust the signal parameters accordingly.

Referring again to FIG. 1, the external system 140 may include any computing device with at least one processor and memory, and capable of receiving, sending, and processing instructions associated with the operation of the FES system 102. The external system 140 may be directly attached to the FES system 102, via a USB connection, or may connect remote with the FES system 102 as long as the external system 140 can communicate with the FES system 102 via the public network 160 or the system network 150.

It will be understood that although only one external system 140 is illustrated in FIG. 1, multiple external systems 140 may interact with the FES system 102 at one time. The number of external systems 140 that may interact with the FES system 102 at a given time may be limited by the data transmission capacity of the system network 150 and the public network 160.

The external system 140 may be an electronic tablet device, a personal computer, a workstation, a server, a portable computer, a mobile device, a personal digital assistant, a laptop, a smart phone, a WAP phone, an interactive television, video display terminals, gaming consoles and portable electronic devices or any combination of these.

Data associated with the usage of the FES system 102 by the user 170 may be transmitted to the external system 140 via the system network 150 or the public network 160. A third party, such as a doctor, clinician or other medical personnel, may access the external system 140 to retrieve the usage data. Based on the usage data, the third party may decide to vary and update certain signal parameters associated with the stimulation signal currently generated by the stimulation unit 110. The external system 140 may then transmit the updated signal parameters to the FES system 102 via the system network 150 or the public network 160.

The external system 140 may also include any device capable of measuring various physiological parameters, such as heart rate and blood oxygen levels. These devices may be worn or carried by the user 170 or attached to at least one unit of the FES system 102. Any physiological information received by the FES system 102 may be analyzed and used for adjusting signal parameters of the stimulation signals. For example, the physiological information may indicate that the heart rate of the user 170 exceeds a recommended heart rate threshold and the FES system 102 may respond by decreasing an intensity of the stimulation signal or even terminating the stimulation signal in order to minimize any risk of injury. The physiological information received by the FES system 102 may also be stored at the FES system 102 or at a remote storage system.

The system network 150 includes any network capable of carrying data between each of the stimulation unit 110, the sensor unit 120 and the controller unit 130, as well as between the FES system 102 and the external system 140. System network 150 may include one or more wireless communication networks, such as Wireless LAN (WLAN), a local area network implemented by using technologies such as, but not limited to Bluetooth™ technology or infrared light and other networks implemented using similar protocols and technologies. The system network 150 may also include multiple sub-networks.

Networks implemented using Bluetooth™ technologies may be Personal Area Networks (PAN) and can provide enhanced security in comparison with other wireless networks. It is well known that a Bluetooth™ communication network is capable of exchanging data between different devices over short distances using short-wavelength radio transmissions in the ISM radio band of 2,400 to 2,480 MHz.

Due to the multiple different units within the FES system 102 that may be required to communicate with each other, the FES system 102 may require multi-point connections. When the system network 150 is implemented with Bluetooth technology, the system network 150 may facilitate multi-point connections by entering a special command mode in which two different protocols are used. The two different protocols include the standard Bluetooth communication protocol and an FES system protocol that converts data provided in the standard Bluetooth communication protocol into data recognizable by each of the different units within the FES system 102.

In a command mode, any data received by system network 150 is first interpreted based on the standard Bluetooth communication protocol. Based on the standard Bluetooth communication protocol, the received data is processed and encapsulated with extra bytes in order to match data traditionally provided in the command mode. The processed data can then be interpreted using the FES system protocol.

In embodiments in which the system network 150 is implemented using Bluetooth technology, the FES system 102 may operate to minimize errors in data transmission caused by environmental factors.

The public network 160 can include any network capable of carrying data between the external system 140 and the FES system 102. Generally, the public network 160 may be any communication network that is used as the system network 150. However, unlike the system network 150, the public network 160 may also facilitate communication for the external system 140 when it is outside of the range of a wireless network. For example, the public network 160 may include the Internet, Ethernet, a plain old telephone service (POTS) line, a public switch telephone network (PSTN), an integrated services digital network (ISDN), a digital subscriber line (DSL), coaxial cable, fiber optics, satellite, mobile, wireless (e.g. Wi-Fi, WiMAX), SS7 signaling network, fixed line, local area network, wide area network, and others, including any combination of these.

As described, the sensor unit 120 includes sensors that detect motion information and environmental data. Based on the detected sensor data, the sensor unit 120 may define parameters for the stimulation signal to adjust an orientation of the foot and as a result, improve the gait of the user 170. The components of the sensor unit 120 will now be further described with reference to FIGS. 4 to 8C.

Figure 4:
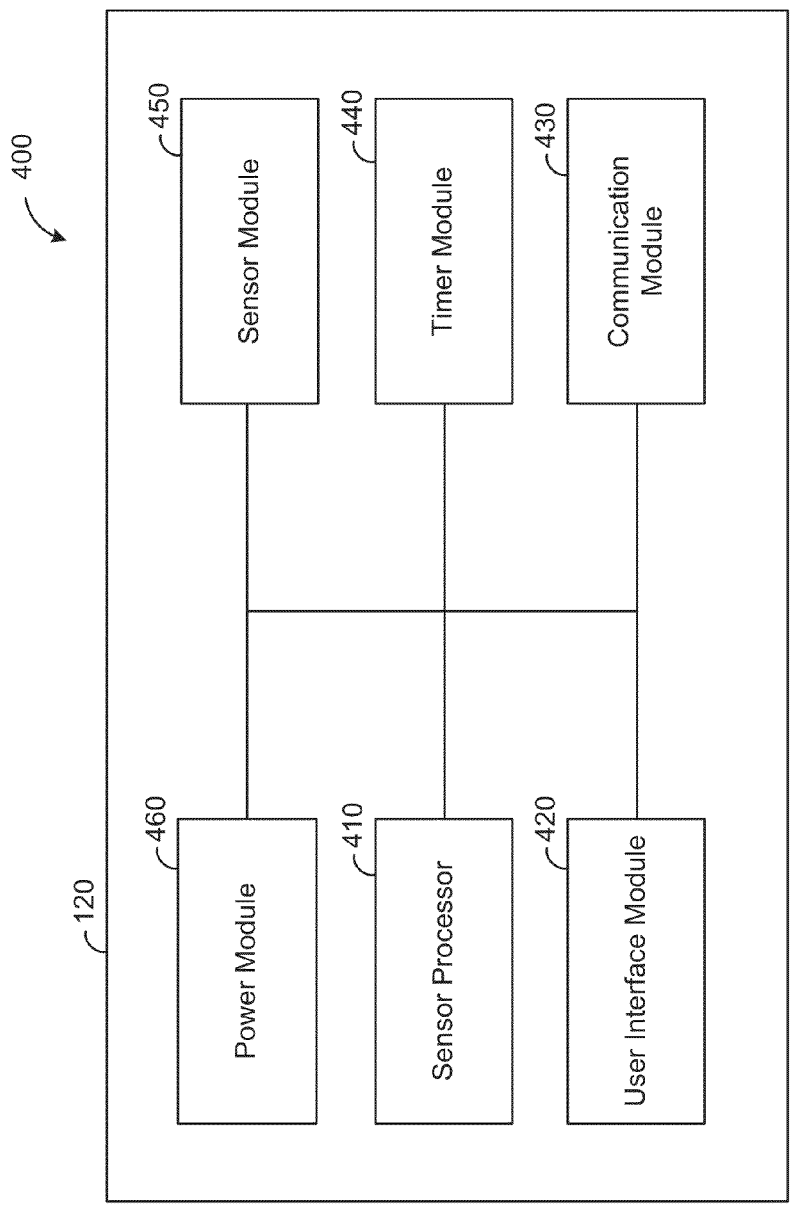
FIG. 4 illustrates a block diagram of a sensor unit of the FES system in accordance with an example embodiment.

Referring now to FIG. 4, which illustrates an example block diagram 400 of a sensor unit 120. As shown in FIG. 4, the sensor unit 120 includes a sensor processor 410, a user interface module 420, a communication module 430, a timer module 440, a sensor module 450 and a power module 460.

The sensor processor 410 may operate each of the various modules in the sensor unit 120 for implementing the methods described herein. For example, sensor processor 410 can receive motion information and environmental data collected by the sensor module 450, and determine a foot condition based on the detected sensor data. The sensor processor 410 may also format any collected sensor data into an output format that is suitable for each of the stimulation unit 110 and controller unit 130. For example, the sensor processor 410 may format the collected sensor data into a hexadecimal byte form. The sensor processor 410 may also operate with the communication module 430 and the timer module 440 for transmitting formatted sensor data to the stimulation unit 110, the controller unit 130 and the external system 140 at the appropriate time. For example, the sensor processor 410 may trigger the transmission of the sensor data from the sensor unit 120 at the start of the lift period (i.e. when the user 170 is just starting to lift their foot).

The communication module 430 can act as an interface between the sensor unit 120 and components external to the sensor unit 120. The communication module 430 can enable interaction between the sensor unit 120 and each of the controller unit 130 and the stimulation unit 110. If needed, the communication module 430 can also enable interaction between the sensor unit 120 and the external system 140. The communication module 430 can facilitate wireless communication via the system network 150, for example. The wireless communication may be based on Bluetooth technology or other wireless communication protocols and technologies, such as, but not limited to, WLAN or WPAN.

In some embodiments, the communication module 430 may also include a Universal Serial Bus (USB) interface for facilitating transfer of data from the sensor unit 120 to other components, such as the controller unit 130 and the external system 140 by a direct USB connection.

The timer module 440, as described, can track the passage of time. For example, the timer module 440 may measure the lift period for the user 170 so that the parameters of the stimulation signal can be customized for that user 170. Also, if data collection is based on predetermined time intervals, the timer module 440 can facilitate collection of sensor data by tracking the passage of time and indicating when the predetermined time interval has elapsed.

The sensor module 450 includes various different sensors, such as a gyroscope, an accelerometer, a compass, a force sensor and a temperature sensor, for collecting motion information and environmental data. The sensor module 450 can collect motion information, such as three-axis angular velocity from the gyroscope, three-axis acceleration from the accelerometer and pressure from the force sensor, and environmental data, such as temperature, and provide the collected information and data to other modules in the sensor unit 120, such as sensor processor 410 or communication module 430, for further processing. In some embodiment, some of these sensors can be optional such as the temperature sensor and the compass.

The compass can be a three-axis compass that detects and generates geomagnetic fields at each of the x-axis, y-axis and z-axis in the Cartesian coordinate system. The geomagnetic field is measured with the unit Tesla. The compass is used to determine the heading of the user 170 during movement.

The force sensor detects the amount of pressure it receives, such as the amount of pressure that is exerted by the foot of the user 170. The pressure is measured with the unit Newton (N). In some embodiments, data provided by the force sensor may be used for indicating a start of the lift period. In response to detecting the start of the lift period, the sensor processor 410 may trigger the timer module 440 to monitor the passage of time to determine the lift period. The sensor processor 410 may also notify the stimulation unit 110 via the communication module 430, for example, that the foot of the user 170 has left the ground.

The temperature sensor measures a temperature of the surrounding of the user 170. The measured temperature may be used for compensating for variations in the data collected by the other sensors in the sensor module 450 that may have been caused by the temperature of the surrounding. The temperature may be measured in Celsius or Fahrenheit.

The gyroscope can be a three-axis gyroscope that detects and generates an angular velocity at each of the x-axis, y-axis and z-axis in a Cartesian coordinate system. The angular velocity is measured using degrees or radians. Similarly, the accelerometer can be a three-axis accelerometer that detects and generates acceleration information at each of the x-axis, y-axis and z-axis in the Cartesian coordinate system. The amount of acceleration can be provided as a rate at which a velocity of the user 170 changes with time and a normalized gravitational acceleration value (in multiples of the standard gravity, or g).

In some embodiments, the gyroscope and the accelerometer may be provided together in an integrated circuit, such as in an inertial measurement unit (IMU). The IMU is an advanced micro-electro-mechanical system (MEMS) that consists of at least a gyroscope and an accelerometer.

Figure 5:
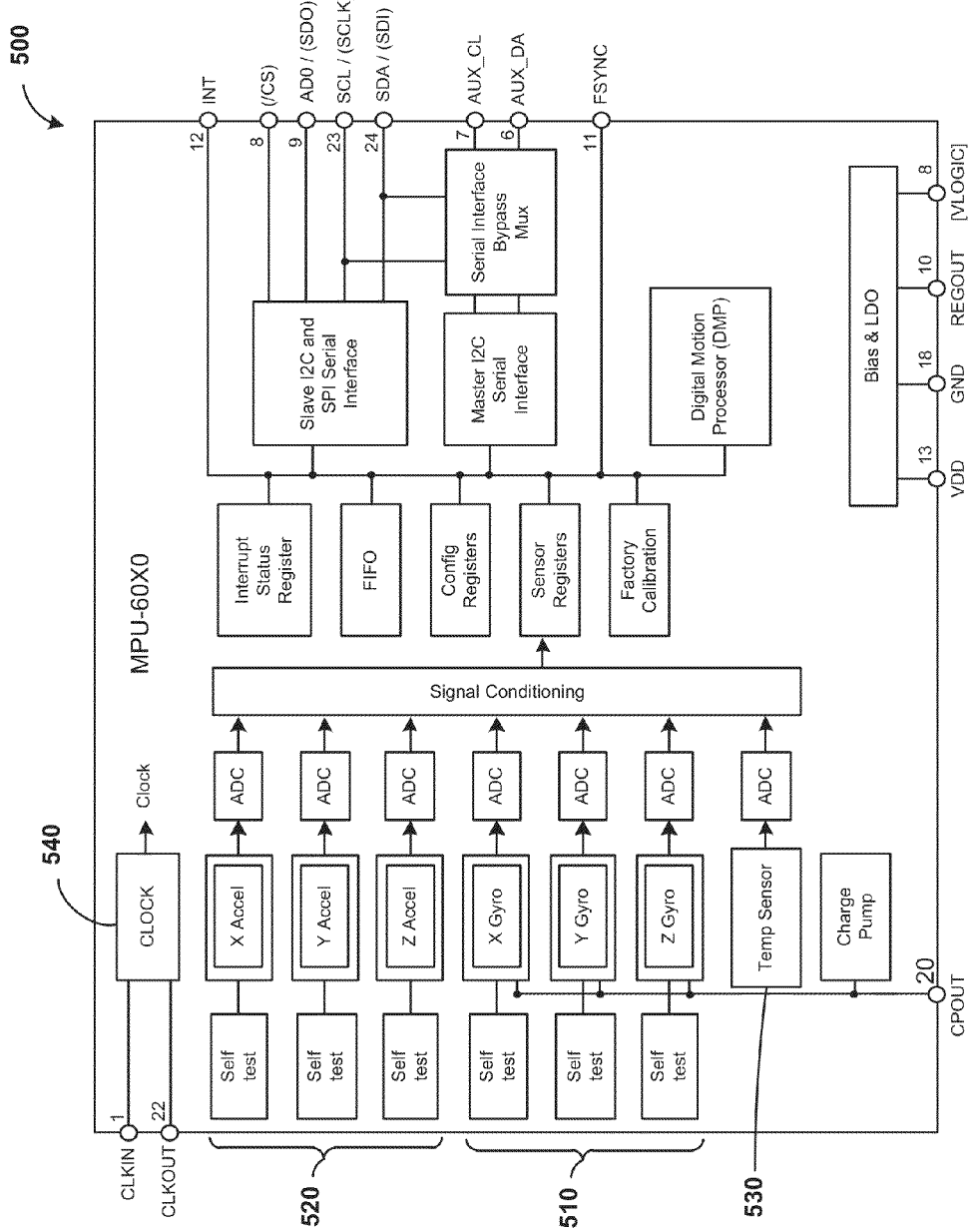
FIG. 5 illustrates a block diagram of an inertial measurement unit (IMU) that can be used in the sensor unit in accordance with an example embodiment.

A block diagram of an example IMU 500 is illustrated in FIG. 5. As shown in FIG. 5, the IMU 500 includes a three-axis gyroscope 510, a three-axis accelerometer 520 and a temperature sensor 530. The IMU 500 also includes a timing clock 540. The IMU 500 can generate a real-time angular velocity and acceleration of the foot of the user 170 where the sensor unit 120 is located.

The use of the IMU 500 in the sensor module 450 can offer several advantages over the use of gyroscopes and accelerometers that are in separate physical components. For instance, the number of hardware components is minimized with the integrated design of the IMU 500. As a result, the size and cost of the IMU 500 is less than if separate gyroscopes and accelerometers are used. Power consumption is also smaller in the IMU 500 than if multiple separate circuits are used. There is also increased stability in data collected from the IMU 500 since data collected from separate gyroscopes and accelerometers require synchronization. Also, the debugging of one circuit, as in the case of the IMU 500, is easier than having to debug multiple circuits in the case of physically separate gyroscopes and accelerometers.

Referring again to FIG. 4, the power module 460 can include a power regulator for monitoring power consumption of the sensor unit 120. The power regulator helps ensure that a stable and reliable power is being provided to the other modules in the sensor unit 120. The power module 460 may also include a charge monitor for managing the current and voltage of the sensor unit 120 when the sensor unit 120 is being charged. In some embodiments, the power module 460 may operate with the communication module 430 for receiving power via a USB interface (when available). The power module 460 may also operate based on commands received from other modules in the sensor unit 120. For example, the power module 460 may be triggered to exit the sleep mode in response to a wakeup signal received from the user interface module 420, such as when a wake button is activated or the user 170 starts to move.

The user interface module 420 may receive inputs from the user 170 via buttons or other user controls provided at a user interface of the sensor unit 120. For example, a reset button can be provided at the user interface such that when activated by user 170, the user interface module 420 receives a signal indicating that sensor unit 120 should be restarted. The user interface can also include various displays and indicators for providing user 170 with operation information associated with sensor unit 120 as provided via the user interface module 420. For example, the user interface can include LEDs for indicating different operation modes or operation status of the FES system 102.

Figure 6:
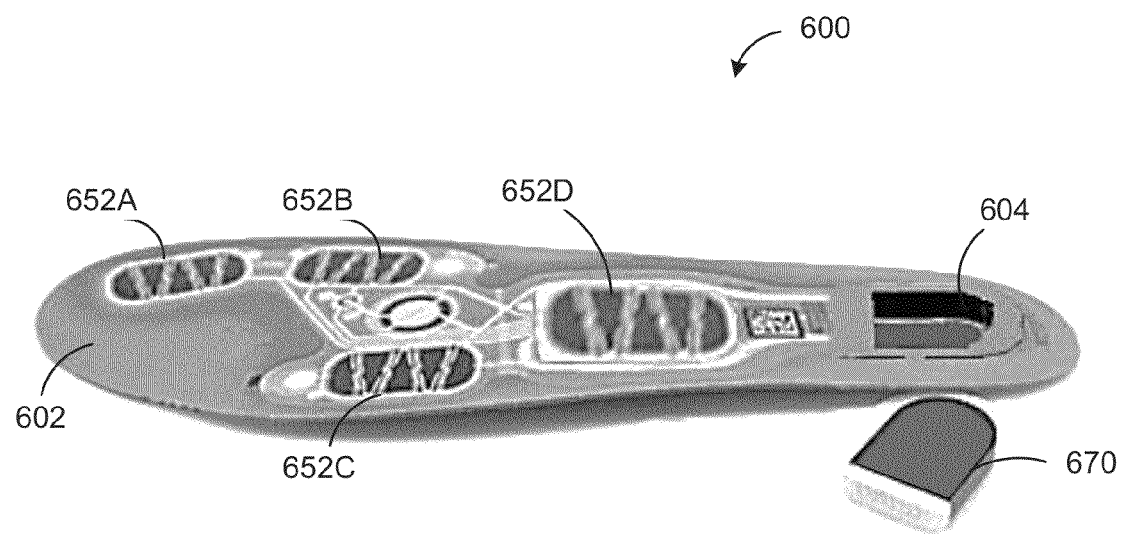
FIG. 6 illustrates an example configuration of the sensor unit.
Figure 7B:
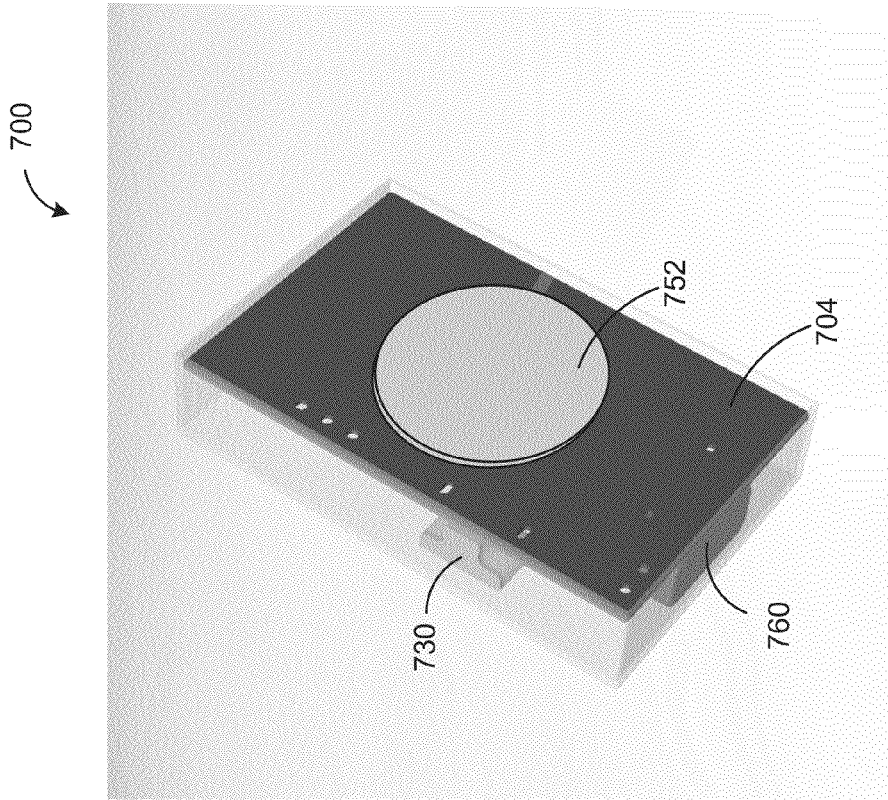
FIGS. 7A and 7B illustrate another example configuration of the sensor unit.
Figure 7A:
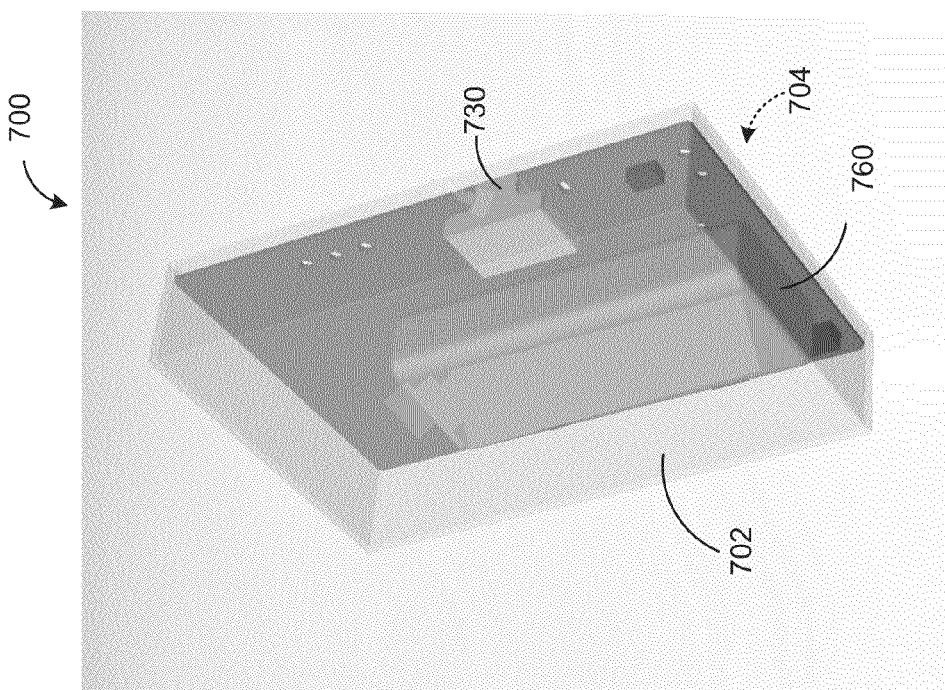

FIGS. 6, 7A and 7B show example configurations of the sensor unit 120.

FIG. 6 illustrates an example sensor configuration 600 with the sensor unit 120 embedded in an insole 602 of a footwear. The sensor unit 120 in sensor configuration 600 includes multiple force sensors 652, such as force sensors 652A to 652D, that are distributed throughout the insole 602 and a sensor unit socket 604. By including multiple force sensors 652 that are distributed throughout the insole 602, the sensor unit 120 can detect an increased number of foot orientations and movements with increased accuracy. Data provided by each of the force sensors 652 to the sensor processor 410 includes a measured force amount and a force sensor identifier for identifying the corresponding force sensor 652. The sensor processor 410 can determine the foot orientation based on data collected by each of the force sensors 652 and a location of the corresponding force sensor 652 in the insole 602. The location of each force sensor 652 may be determined from the force sensor identifier.

The sensor unit socket 604 can receive a component, such as 670, that houses the other modules of the sensor unit 120, such as the power module 460, the sensor processor 410, the timer module 440, other sensors in the sensor module 450 (e.g., accelerometer, gyroscope, etc.), the user interface module 420, and the communication module 430. By separating the force sensors 652 from the other modules in the sensor unit 120, the other modules can be protected from unnecessary wear that results from use of the sensor unit 120.

FIGS. 7A and 7B are different views of another example sensor configuration 700 of the sensor unit 120. The sensor configuration 700 may be the component 670 and placed in the sensor unit socket 604 of FIG. 6, or may be attached to the footwear of the user 170.

The sensor configuration 700 includes an upper wall 702 and a bottom wall 704 opposite from the upper wall 702. As shown in FIG. 7B, a power module 760 and a USB interface 730 are located on a first surface of the bottom wall 704, and a force sensor 752 is located on a second surface of the bottom wall 704. The second surface of the bottom wall 704 faces the upper wall 702.

Sensor components in existing FES systems tend to be heavier (e.g., a weight of 27 g to 35 g) and larger in size (e.g., a height of 48 mm to 80 mm, a width of 40 mm to 50 mm and a thickness of 10 mm to 21 mm). The dimensions of the described sensor units 120, on the other hand, are generally lighter and smaller. For example, the dimensions of the sensor unit 120 in sensor configuration 700 may be 20 mm to 42 mm in height, 15 mm to 27 mm in width and 10 mm in thickness. Other similar dimensions may be used for the sensor unit 120. In some embodiments, the sensor unit 120 in sensor configuration 700 may have a weight of 15 g to 25 g.

Figure 8B:
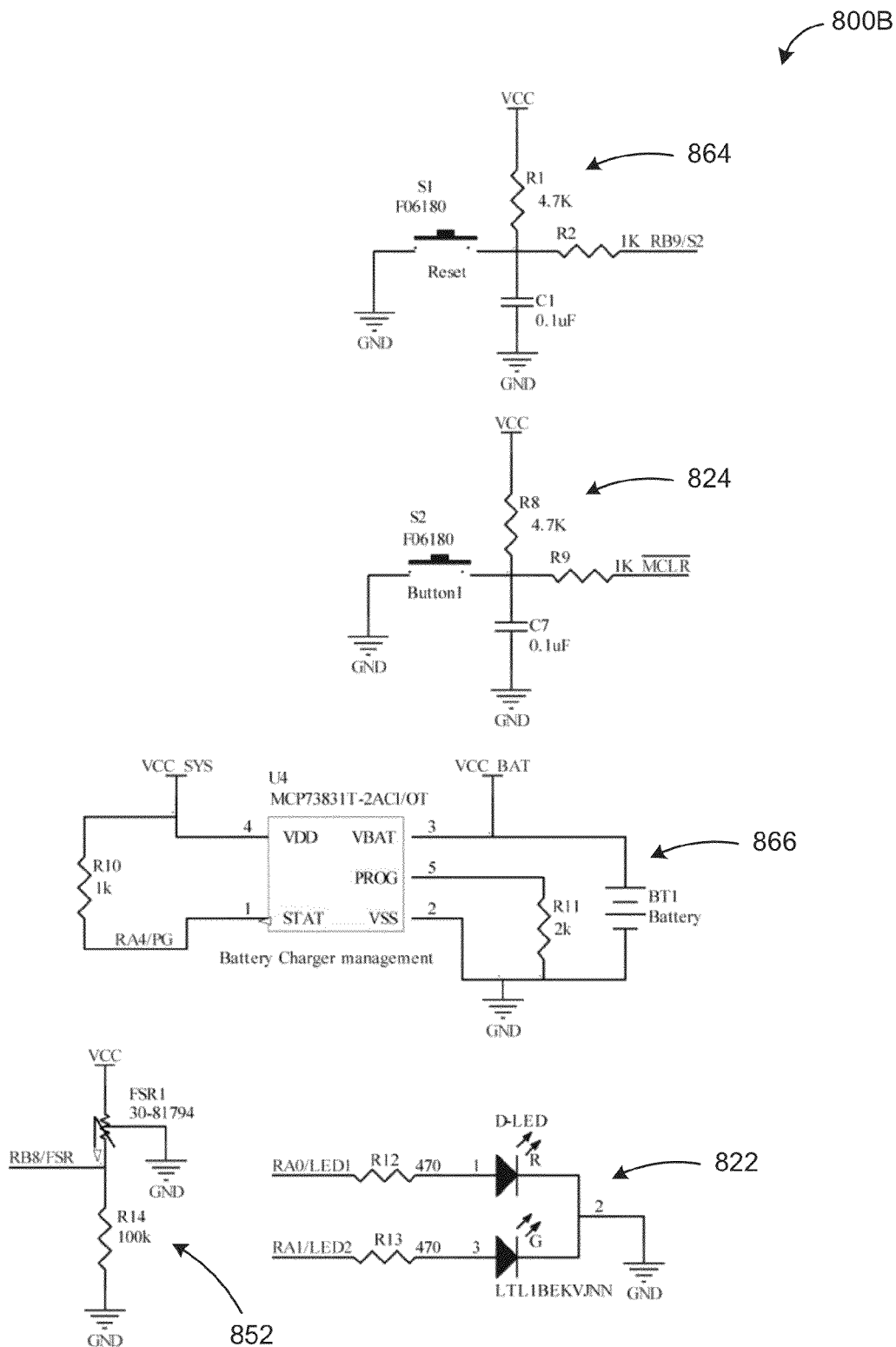
Figure 8C:
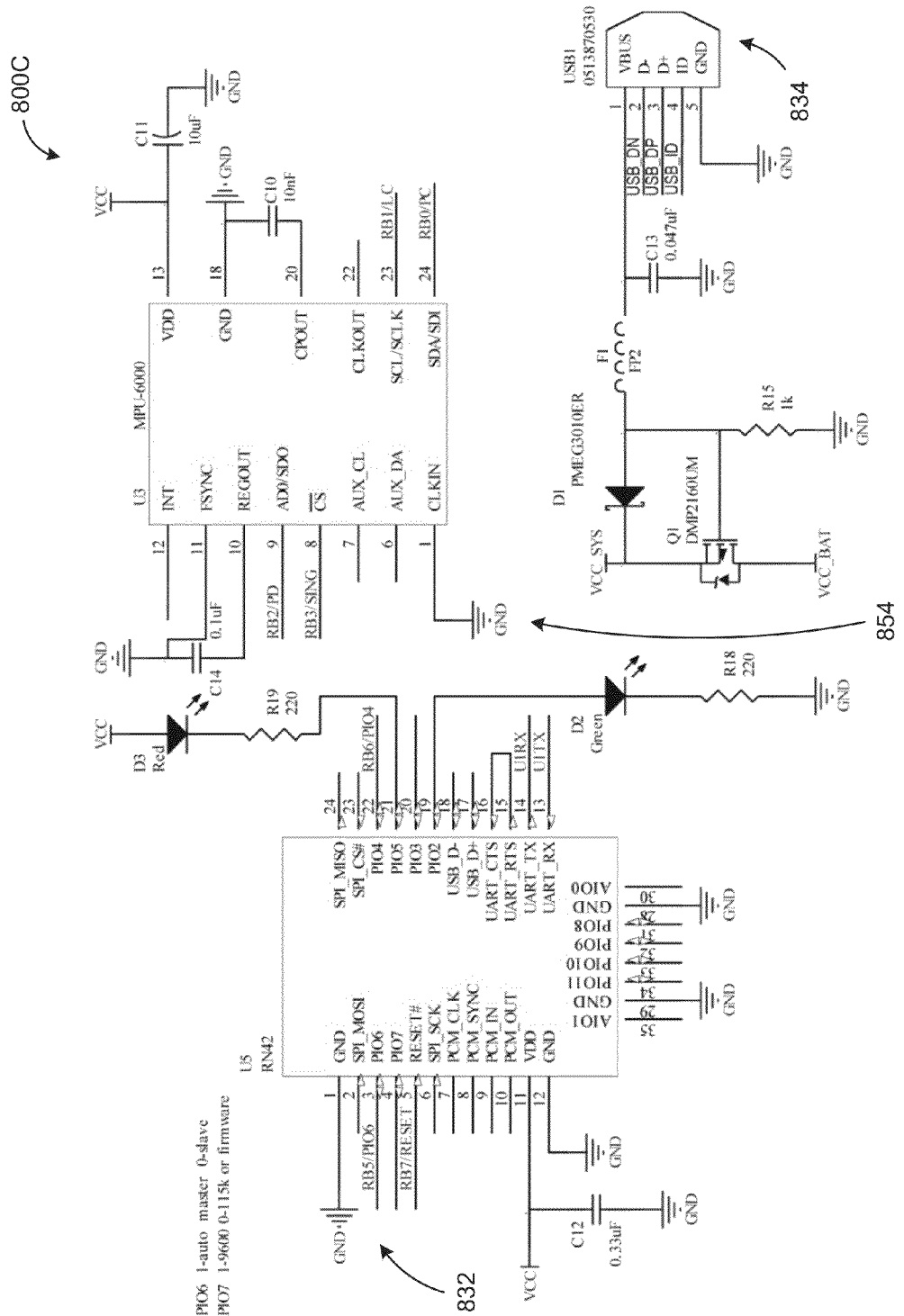

An example circuit design 800 of the sensor unit 120 is shown in FIGS. 8A-8C showing circuit portions 800A, 800B and 8000. The circuit design 800 includes a sensor processor 810, an LED 822, a reset button 824, a Bluetooth radio 832, a USB interface 834, a force sensor 852, an IMU 854, a power regulator 862, a wakeup button 864, and a charge monitor 866. The LED 822 may indicate a status of the sensor unit 120. For example, the LED 822 is red when there is an error at the sensor unit 120, the LED 822 is green when the sensor unit 120 is operating normally and the LED 822 is brown when the sensor unit 120 is in sleep mode. The functionality and operation of the other components in circuit design 800 has been described with reference to FIGS. 1 and 4. It will be understood that different designs of the sensor unit 120 may be used and that the circuit design 800 is only provided for illustrative purposes.

Figure 9:
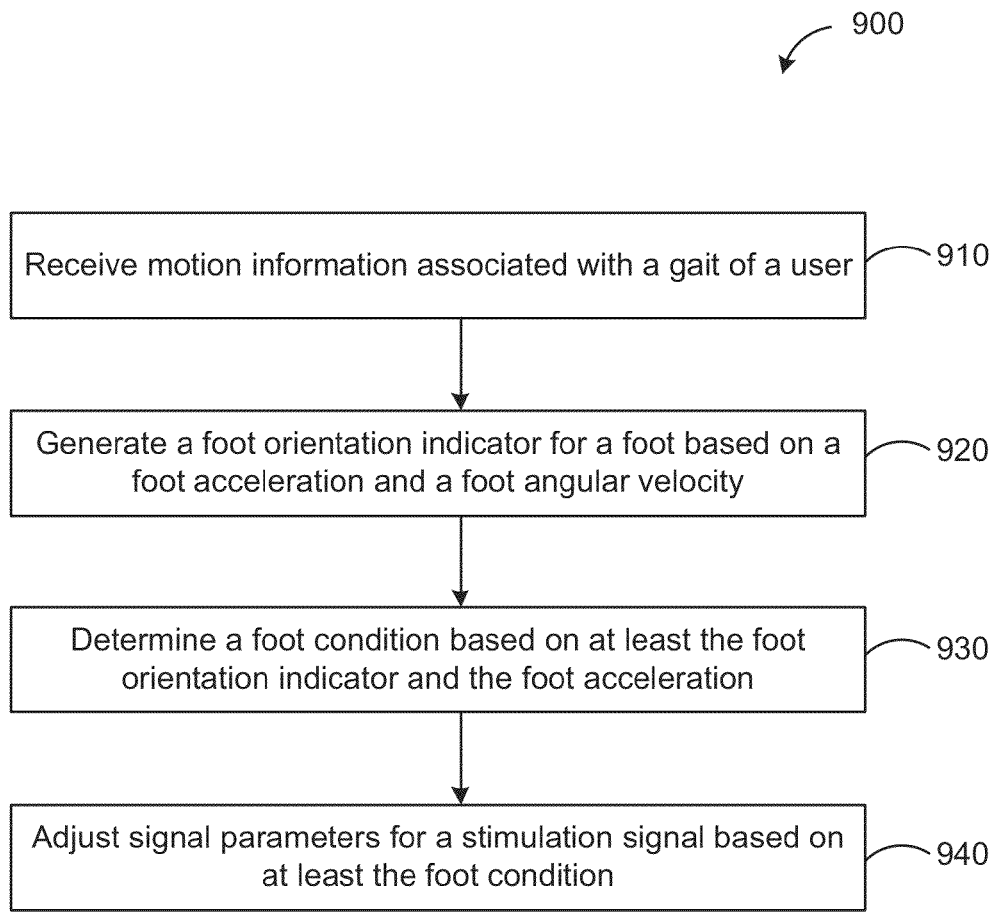
FIG. 9 is a flowchart of an example embodiment of a method of improving a gait of a user using the FES system described herein.
Figure 10:
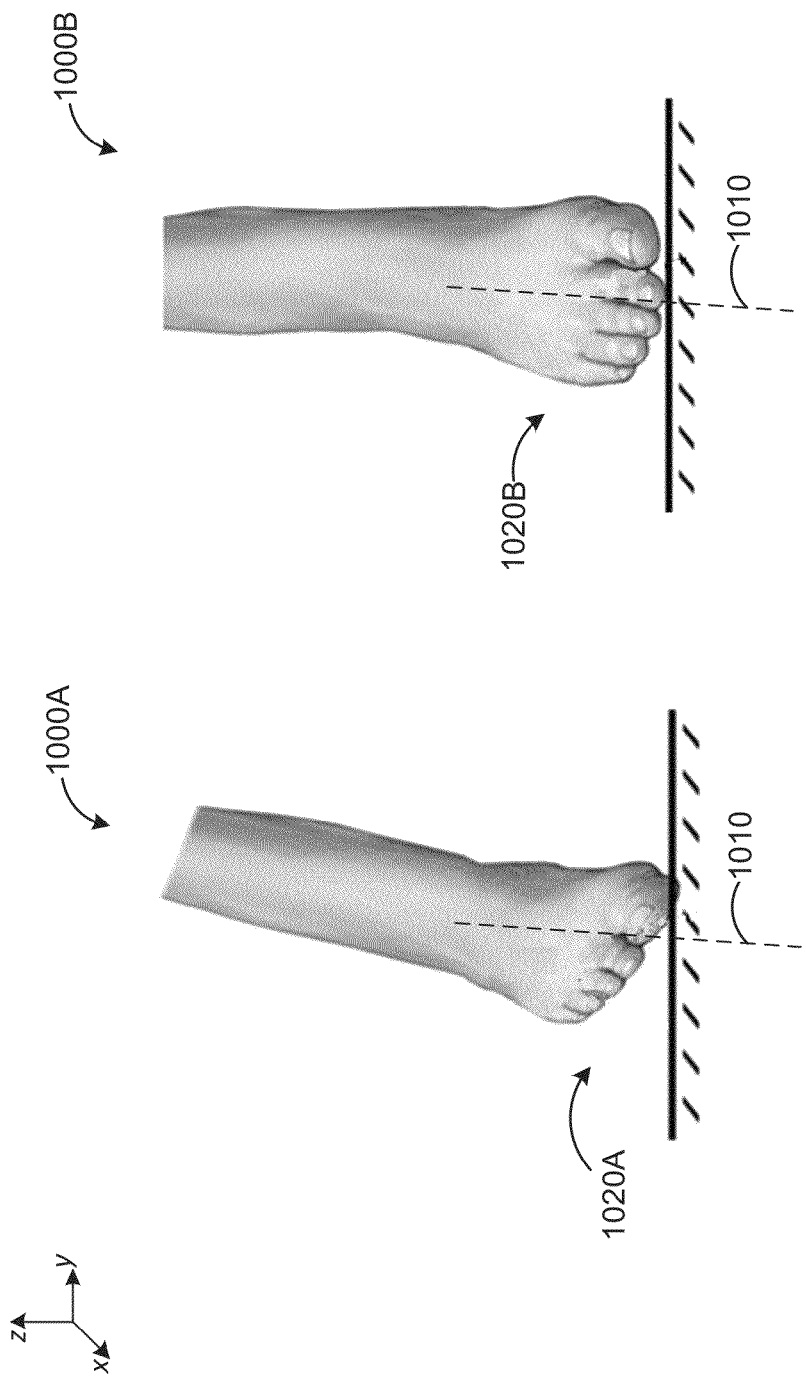
FIGS. 10A and 10B illustrate example embodiments of foot orientations.

Simultaneous reference will now be made to FIGS. 9, 10A and 10B for describing example embodiments of improving the gait of the user 170. FIG. 9 is a flowchart 900 of an example method of improving the gait of the user 170 with the FES system 102. FIGS. 10A and 10B illustrate example embodiments of foot orientations 1000A and 1000B, respectively, for a foot of the user 170. FIGS. 10A and 10B are provided with respect to a three-dimensional Cartesian coordinate system. It will be understood that other coordinate systems may similarly be used.

At 910, the sensor processor 410 receives motion information associated with the gait of the user 170. The sensor module 450 includes sensors that can collect, at least, motion information. The sensors may continuously or periodically collect motion information or may be triggered to collect motion information. The motion information can include a foot acceleration of the foot of the user 170 and a foot angular velocity of the foot of the user 170.

The foot acceleration represents a rate at which a velocity of the foot changes with time. The foot acceleration may be provided by the accelerometer in the sensor module 450 or the IMU 500. A static angular position of the foot may be determined based on the foot acceleration.

The foot angular velocity represents a rate of change of angular displacement of the foot of the user 170. The foot angular velocity may be provided by the gyroscope in the sensor module 450 or the gyroscope 510 in the IMU 500. The foot angular velocity can be provided as a vector value that includes an angular speed of the foot and a direction indication corresponding to an axis of rotation.

In some embodiments, the motion information can include a force amount indicating an amount of force exerted by the foot on the sensor module 450 as the user 170 walks. The force amount can be detected by the force sensor 652 or 752, for example. The sensor module 450 may transmit the force amount to the sensor processor 410 only when the force amount exceeds a force threshold (e.g. a certain magnitude). The force threshold helps the sensor processor 410 to avoid detection of false motions, such as shifting of weight by the user 170 from one foot to the other. These false motions are generally not considered movements that require the assistance of the FES system 102. The force threshold may be in the range of 200N to 300N. The force threshold may, in some embodiments, be at least 294N, which generally corresponds to half of a gravitational force for an individual weighing 60 kg.

After the sensor module 450 collects the motion information, the sensor module 450 may transmit the motion information to the sensor processor 410. The sensor module 450 may transmit the motion information continuously, periodically or in response to receiving a triggering event. The triggering event may be due to one or more predetermined events, such as a significant change in the collected motion information (e.g., the change of a given element of motion information exceeds a threshold amount) or a time interval. For example, the sensor module 450 may be configured to transmit the motion information to the sensor processor 410 at every 10 ms interval. It will be understood that other time intervals, or even multiple different time intervals, may be similarly used.

The sensor module 450 may also collect environmental data associated with a surrounding of the user 170. Similar to motion information, the sensor module 450 may also transmit the environmental data continuously, periodically or in response to a triggering event. Similar to motion information, triggering events for collection of the environmental data may also be predetermined events or timed intervals.

The environmental data may include a temperature of the surrounding. The sensor module 450 may transmit the temperature information to the sensor processor 410 only when the temperature exceeds a temperature threshold. The temperature threshold may be used as a safety mechanism to ensure that the sensor unit 120 does not operate in severe temperature conditions. The temperature threshold may include an upper temperature threshold and a lower temperature threshold. The upper threshold may be at least 60° C. and the lower threshold may be at least less than −20° C.

It will be understood that other motion information and environmental data may also be collected by the sensor unit 120 in alternative embodiments.

At 920, the sensor processor 410 generates a foot orientation indicator for the foot based on the foot acceleration and the foot angular velocity. The foot orientation indicator corresponds to an angular position relative to a longitudinal axis of the foot. The angular position may be generated based on an orientation of the foot with respect to the longitudinal axis of the foot. For example, as will be described with reference to FIGS. 12A and 12B, the angular position may correspond to various angles measured in the three-dimensional Cartesian coordinate system.

As shown in FIGS. 10A and 10B, the longitudinal axis 1010 for the foot is provided along the x-axis and is common for both foot orientations 1000A and 1000B. In FIG. 10A, the foot orientation 1000A corresponds to an angular position 1020A in which the foot is oriented away from the y-axis and towards the positive z-axis direction. The foot orientation indicator of the foot illustrated in FIG. 10A corresponds to the angular position 1020A. The foot orientation 1000B of the foot shown in FIG. 10B, however, is associated with an angular position 1020B that is generally parallel to the y-axis. The foot orientation indicator of the foot illustrated in FIG. 10B corresponds to the angular position 1020B.

Accurately determining the angular position 1020 can be difficult. Use of one tilt sensor is unlikely sufficient to determine the angular position 1020. Gyroscopes, for example, are unable to collect accurate motion information of an object when that object is still. When the object is still, the corresponding angular velocity is zero and the gyroscope considers the position of the object to be horizontal. The gyroscope cannot determine an absolute angle position without an absolute reference. Accelerometers, on the other hand, are unable to distinguish between acceleration and gravity when that object is in motion.

Accordingly, the sensor processor 410 may determine the foot orientation indicator by relying on data collected by multiple sensors. For example, the sensor processor 410 may rely on data from both a gyroscope and an accelerometer to generate the foot orientation indicator. Since gyroscopes are unable to accurately determine the angular position 1020 of the object when the object is in motion and accelerometers are unable to accurately determine the angular position 1020 when the object is still, the sensor processor 410 may determine the foot orientation indicator by compensating data determined based on the foot angular velocity (e.g., data from gyroscope) with data determined based on the foot acceleration (e.g., data from accelerometer).

Figure 11:
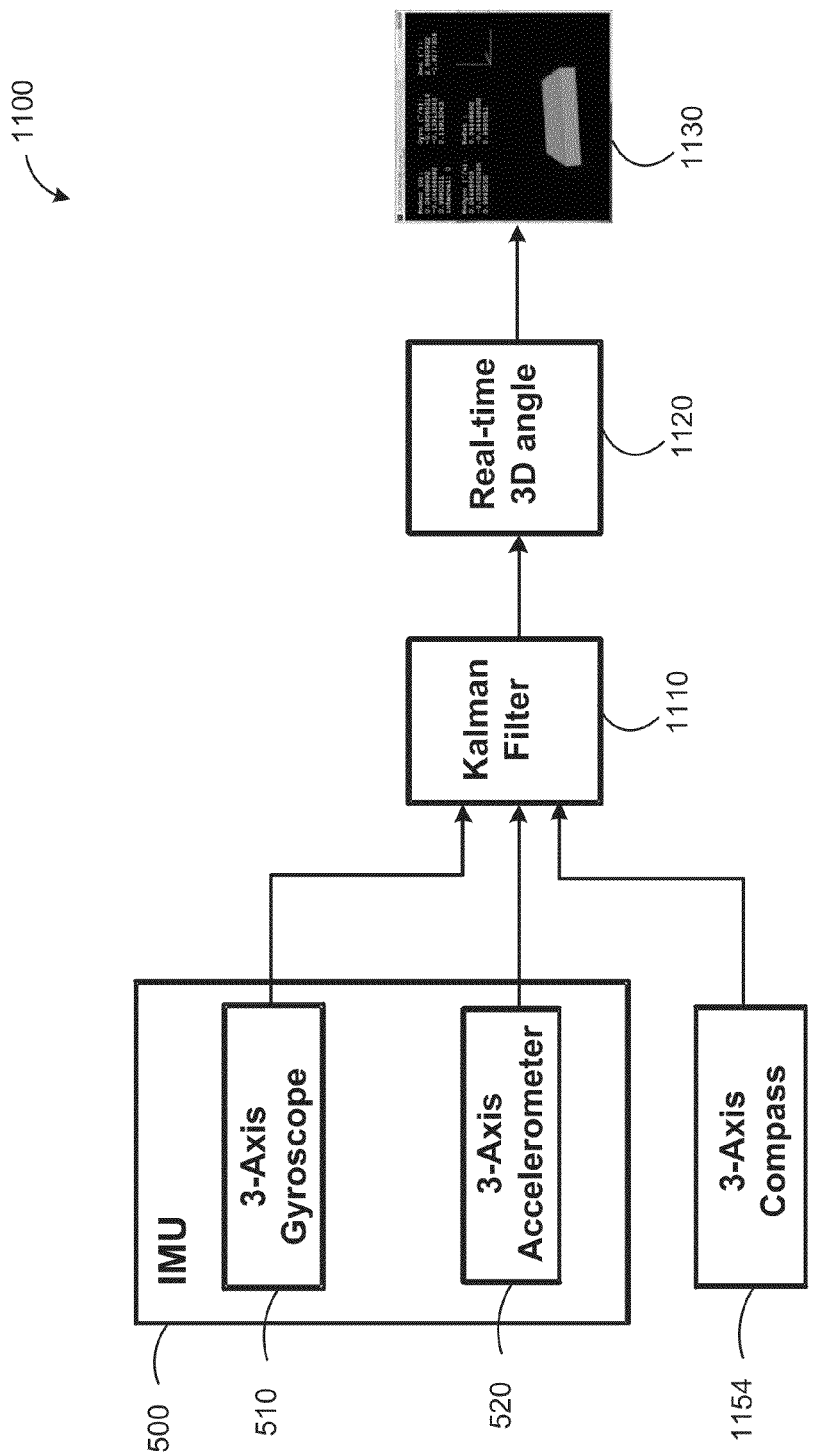
FIG. 11 illustrates an example embodiment of a method of applying a Kalman filter to data collected by the sensor unit.

Reference will now be made to FIG. 11, which illustrates an example method 1100 of applying of a Kalman filter to data collected from the sensor module 450 for generating a real-time three-dimensional angle. In some embodiments, the sensor processor 410 may apply the Kalman filter 1110 to the collected motion information, such as data collected from each of the three-axis gyroscope 510 and the three-axis accelerometer 520 of the IMU 500 and data from a three-axis compass 1154 in the sensor module 450, for generating a real-time three-dimensional angle 1120. The three-dimensional angle may be applied for generating a system model 1130 for the foot of the user 170.

In some embodiments, the Kalman filter may also be applied for compensating data determined based on the foot angular velocity with data determined based on the foot acceleration. The Kalman filter may also filter the collected motion information to remove any noise or other inaccuracies.

Figure 12B:
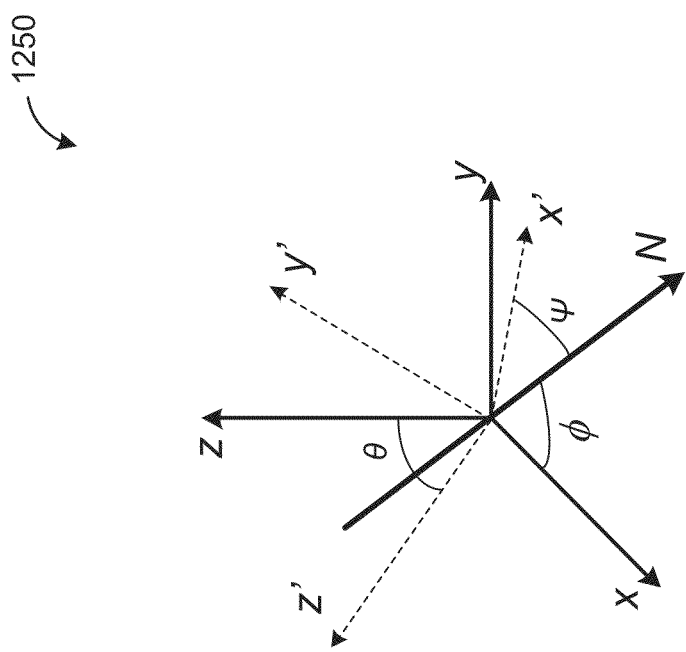
FIGS. 12A and 12B illustrate an example embodiment of a three-dimensional representation for approximating foot orientation.
Figure 12A:
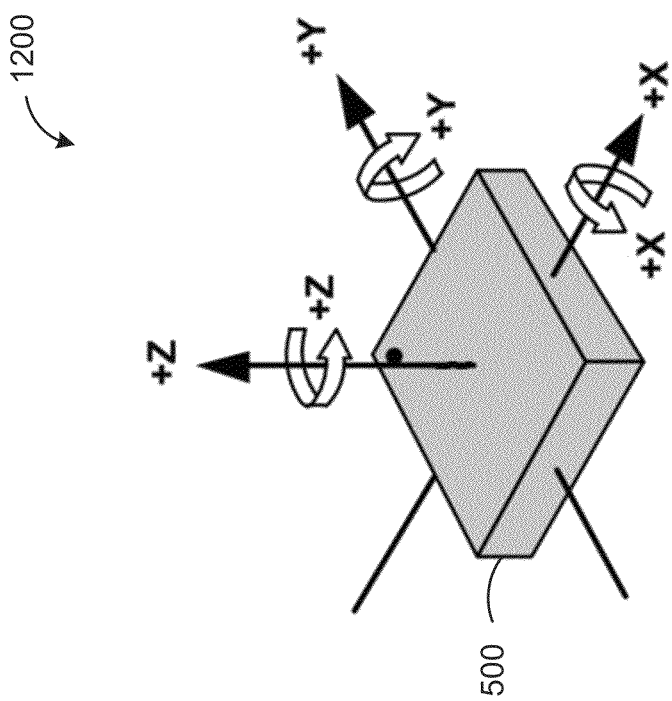

Reference is now made to FIGS. 12A and 12B. FIG. 12A generally illustrates a three-dimensional model 1200 of the foot of the user 170 with reference to the three-dimensional Cartesian coordinate system and FIG. 12B illustrates a representation 1250 of a state variable k for the foot. With reference to FIGS. 12A and 12B, an example Kalman filter process is described for data collected from the IMU 500 and the three-axis compass 1154 based on the state variable k, as represented by equation (1):

$$k = \begin{Bmatrix} \phi \\ \theta \\ \varphi \end{Bmatrix} \quad (1)$$

where, as shown in FIG. 12B, $\phi$ represents a roll value (an angle between the x-axis and the N-axis, or a rotation around the z-axis), $\theta$ represents a pitch value (an angle between the z-axis and the z'-axis, or a rotation around the N-axis), and $\varphi$ represents a yaw value (an angle between the N-axis and the x'-axis, or a rotation around the z'-axis). The x, y and z axes correspond to an initial frame of reference and the x', y' and z' axes correspond to a rotated frame of reference. The N-axis is a line of nodes, which is an intersection of the x-y and the x'-y' coordinate planes.

In some embodiments, the three-dimensional model 1200 of the foot of the user 170 may be provided with reference to an absolute coordinate system. In the absolute coordinate system, a first axis corresponds to North as determined from the three-axis compass 1154, a second axis (G) corresponds to a direction opposite to the direction of gravity and a third axis (W) can then be determined with the use of the right-hand rule with respect to the first axis and the second axis. For example, with respect to FIG. 12A, the first axis may correspond to the positive X-axis and the second axis (G) may correspond to the negative Z-axis. Using the right-hand rule, it can be determined that the third axis (W) corresponds to the positive Y-axis.

As the foot changes in orientation and position, variations of the corresponding angles, $\phi$, $\theta$ and $\varphi$, can be determined with reference to the absolute coordinate system.

In some embodiments, the angular position of the foot, such as 1020A or 1020B, may correspond to at least one of $\phi$, $\theta$ and $\varphi$ as generated by the Kalman filter.

The state variable k can also be represented by equation (2) below:

$$\begin{bmatrix} \dot{\phi} \\ \dot{\theta} \\ \dot{\varphi} \end{bmatrix} = \begin{bmatrix} 1 & \sin\phi\tan\theta & \cos\phi\tan\theta \\ 0 & \cos\phi & -\sin\phi \\ 0 & \sin\phi/\cos\theta & \cos\phi/\cos\theta \end{bmatrix} \begin{bmatrix} p \\ q \\ r \end{bmatrix} \quad (2)$$

where p represents an angular rotational rate with respect to the x-axis, q represents an angular rotational rate with respect to the y-axis, and r represents an angular rotational rate with respect to a z-axis.

In some embodiments, each of the p, q and r values may be provided by a gyroscope, such as the three-axis gyroscope 510.

Based on equations (1) and (2), a state transition model f(k) can be generated for approximating a current state of an angular velocity of a foot with the use of a Kalman filter and based on a previous state of the foot. The state transition model f(k) is illustrated below in equation (3):

$$\begin{bmatrix} \dot{\phi} \\ \dot{\theta} \\ \dot{\varphi} \end{bmatrix} = \begin{bmatrix} 1 & \sin\phi\tan\theta & \cos\phi\tan\theta \\ 0 & \cos\phi & -\sin\phi \\ 0 & \sin\phi/\cos\theta & \cos\phi/\cos\theta \end{bmatrix} \begin{bmatrix} p \\ q \\ r \end{bmatrix} + w \quad (3)$$

$$= \begin{bmatrix} p + q\sin\phi\tan\theta + r\cos\phi\tan\theta \\ q\cos\phi - r\sin\phi \\ q\sin\phi/\cos\theta + r\cos\phi/\cos\theta \end{bmatrix} + w$$

$$= f(k) + w$$

where w represents a process noise.

However, the state transition model f(k) may not be linear. In order to linearize the state transition model f(k), a Jacobian matrix A can be generated from the state transition model f(k), as shown below as equation (4):

$$\begin{bmatrix} p + q\sin\phi\tan\theta + r\cos\phi\tan\theta \\ q\cos\phi - r\sin\phi \\ q\sin\phi/\cos\theta + r\cos\phi/\cos\theta \end{bmatrix} \rightarrow A = \begin{bmatrix} \frac{\partial f_1}{\partial \phi} & \frac{\partial f_1}{\partial \theta} & \frac{\partial f_1}{\partial \varphi} \\ \frac{\partial f_2}{\partial \phi} & \frac{\partial f_2}{\partial \theta} & \frac{\partial f_2}{\partial \varphi} \\ \frac{\partial f_3}{\partial \phi} & \frac{\partial f_3}{\partial \theta} & \frac{\partial f_3}{\partial \varphi} \end{bmatrix} \quad (4)$$

Based on equation (4), a measurement m can be generated based on the state transition model f(k) for approximating the current state of the angular velocity of the foot, such as with equation (5) below:

$$m = \begin{bmatrix} 1 & 0 & 0 \\ 0 & 1 & 0 \\ 0 & 0 & 1 \end{bmatrix} \begin{Bmatrix} \phi \\ \theta \\ \varphi \end{Bmatrix} + v \quad (5)$$

where v represents an observation noise.

Figure 13:
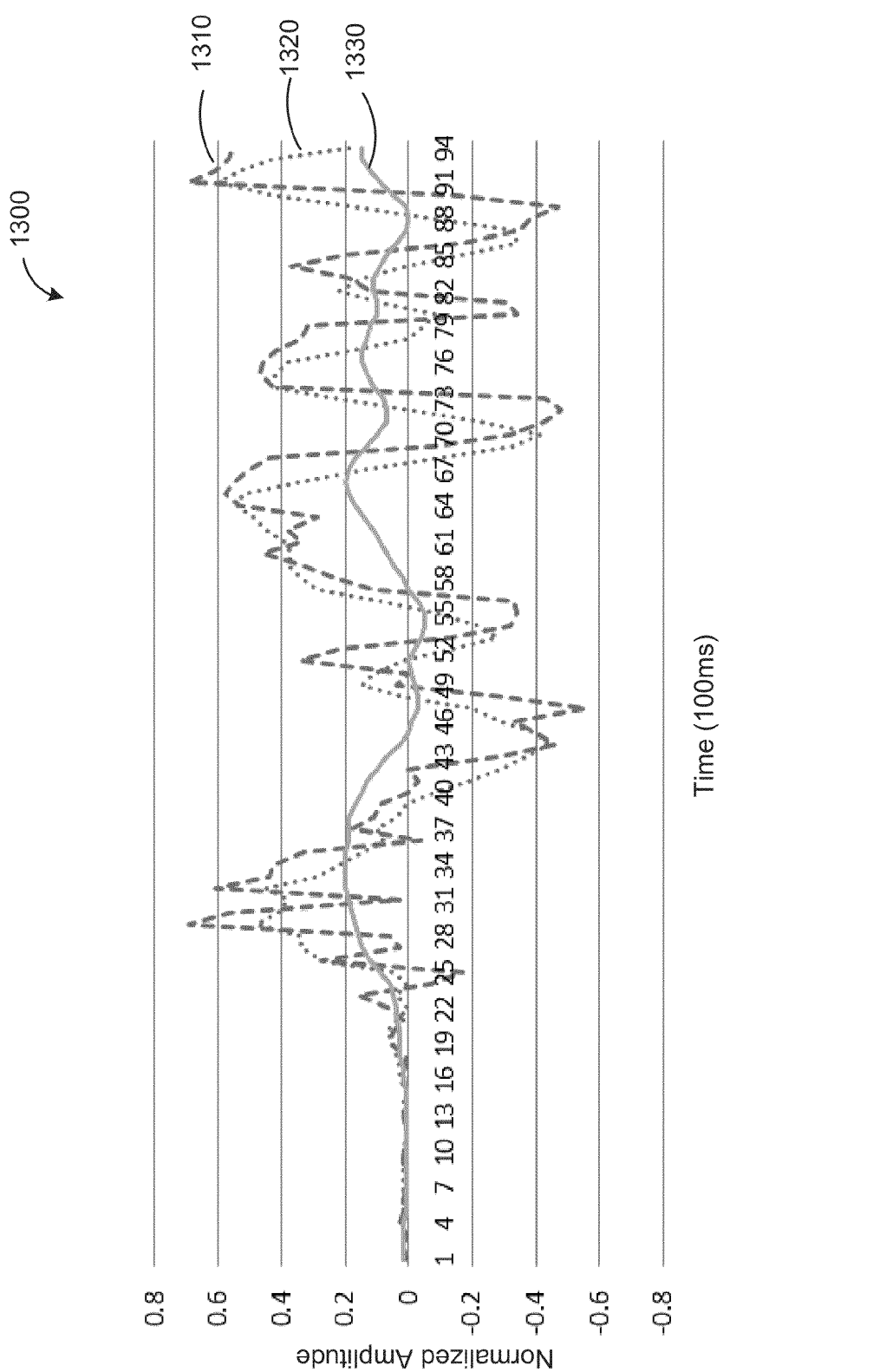
FIG. 13 is a graph of an example of motion information at different data processing stages.

Reference is now made to FIG. 13, which is a graph 1300 illustrating an example embodiment of motion information at different stages of data processing. The motion information illustrated in the graph 1300 is normalized amplitude of the acceleration values generated by combining data from the accelerometer and the gyroscope taken along one direction in a three-dimensional coordinate system. For example, the normalized amplitude represented by the graph 1300 may be taken from the x-axis. Raw motion information provided by the sensor module 450 is shown at 1310. Motion information that has been processed using the Kalman filter is shown at 1330. As illustrated in FIG. 13, the processed motion information 1330 is substantially more stable than raw motion information 1310. Most of the noise and interference signals in the raw motion information 1310 are also eliminated when generating the processed motion information 1330.

In at least some embodiments, the sensor processor 410 may pre-process each of the foot angular velocity and the foot acceleration to improve the accuracy and stability of the collected motion information. For example, the sensor processor 410 may remove extraneous data by applying a recurrence average filter. Referring again to FIG. 13, the pre-processed motion information is shown at 1320. As compared with the raw motion information 1310, the pre-processed motion information 1320 appears to be more stable and less noisy. The Kalman filter can then be applied to the pre-processed motion information 1320.

At 930, the sensor processor 410 determines a foot condition based on at least the foot orientation indicator and the foot acceleration. The foot condition generally indicates the gait quality of the user 170 so that the sensor processor 410 can adjust signal parameters accordingly. The gait quality, as indicated by the foot condition, may be normal or impaired, for example. It will be understood that additional foot conditions may also be used. For example, the impaired condition may be further categorized into various impairments or levels of impairment.

As described, the foot orientation indicator may correspond to the angular position. For embodiments in which the three-dimensional coordinate system of FIGS. 12A and 12B is applied, the foot orientation indicator may include more than one orientation indicators, such as each of $\phi$, $\theta$ and $\varphi$ as generated by the Kalman filter. To determine the foot condition, each change of the values, $\phi$, $\theta$ and $\varphi$, during the gait of the user 170 is compared with an orientation threshold. In some embodiments, a different orientation threshold may be provided for each of the different orientation indicators. For example, a first orientation threshold may be provided for the $\phi$ value, a second orientation threshold may be provided for the $\theta$ value and a third orientation threshold may be provided for the $\varphi$ value. The first orientation threshold, the second orientation threshold and the third orientation threshold may be the same or different as each other.

The sensor processor 410 can determine that the foot condition is a normal condition when the foot orientation indicator is less than an orientation threshold and the foot acceleration is less than an acceleration threshold. When the foot orientation indicator includes more than one orientation indicator, the sensor processor 410 may determine that the foot condition is the normal condition when a majority of the orientation indicators is less than the orientation threshold. A normal condition indicates that the gait quality is satisfactory and therefore, orientation of the foot does not need to be further adjusted to improve the gait. Based on the foot orientation indicator corresponding to the foot orientation 1000B of FIG. 10B, the sensor processor 410 can determine that the foot of the user 170 is in the normal condition.

Alternatively, the sensor processor 410 can determine that the foot is in the impaired condition. The impaired condition indicates that the gait quality is dissatisfactory and therefore, requires improvement. For example, the foot of the user 170 may be experiencing foot drop. The sensor processor 410 can determine that the foot condition is in the impaired condition when at least one of the orientation indicators is greater than or equal to the orientation threshold, or the foot acceleration is greater than or equal to the acceleration threshold. For example, the foot orientation indicator for the foot shown in FIG. 10A corresponds to the angular position 1020A, which is oriented away from the y-axis and towards the positive z-axis direction. If the sensor processor 410 determines that the foot orientation indicator of FIG. 10A is greater than or equal to the orientation threshold, the sensor processor 410 can determine that the foot in FIG. 10A is in the impaired condition. In some embodiments, the sensor processor 410 may determine that the foot condition is in the impaired condition when a majority of the orientation indicators exceed the orientation threshold, or the corresponding orientation threshold(s).

If the sensor processor 410 determines that the foot condition is the impaired condition, the sensor processor 410 can determine signal parameters for adjusting the foot orientation to improve the gait. The sensor processor 410 may continuously monitor the foot condition and update the signal parameters accordingly. In some embodiments, a feedback condition signal may be provided to the sensor processor 410 for indicating whether further adjustment to the signal parameters is required to improve the foot orientation. For the foot illustrated in FIG. 10A, for example, the foot orientation 1000A may be adjusted so that the foot orientation indicator becomes less than the orientation threshold. However, the sensor processor 410 may need to vary the signal parameters one or more times before each direction of the foot orientation indicator is less than the orientation threshold. The determination of the signal parameters based on the determined foot condition will be further described.

Each of the orientation threshold and the acceleration threshold may be predetermined or selected for the user 170 by the third party, such as the doctor or clinician. The orientation threshold may be within a range of 10 to 20 degrees from a previous state of the foot as determined based on an application of the Kalman filter or from the longitudinal axis of the foot. The range of 10 to 20 degrees generally applies for most average users. In some embodiments, the orientation threshold may be approximately 15 degrees, which generally corresponds to an angle of a foot for an average user when that foot is in the normal condition. It will be understood that the orientation threshold may be varied depending on the user 170. The acceleration threshold may be within a range of 1.5 g to 2.2 g. In some embodiments, the acceleration threshold is approximately 1.9 g.

At 940, the sensor processor 410 adjusts signal parameters for the stimulation signal based on at least the foot condition. For the normal condition, the sensor processor 410 may maintain the existing signal parameters. Alternatively, sensor processor 410 may refrain from transmitting any additional signal parameters to either the stimulation unit 110 or the controller unit 130 until the impaired condition is detected.

When the sensor processor 410 determines the impaired condition, the sensor processor 410 may adjust the signal parameters such that the intensity of the stimulation signal is varied to improve the gait quality. The stimulation signal may be varied by a predetermined amount or may be varied by an amount that depends on the data collected by the sensor module 450, such as the motion information and the environmental data.

For example, in response to detecting that the foot in FIG. 10A is in the impaired condition, the sensor processor 410 can adjust the signal parameters in order to improve the gait quality. The sensor processor 410 can adjust the signal parameters based on, at least, the foot orientation indicator, which corresponds to the angular position 1020A, to cause the foot orientation 1000A to be adjusted. The foot orientation 1000A can be adjusted to substantially correspond to the foot orientation 1000B of FIG. 10B.

The sensor processor 410 can adjust the signal parameters based on, at least, an amount in which the foot orientation indicator exceeds the orientation threshold (e.g., an amount at which a direction of the foot orientation indicator exceeds a corresponding orientation threshold) or an amount in which the foot acceleration exceeds the acceleration threshold.

In some embodiments, each of the orientation threshold and the acceleration threshold may include multiple threshold levels. Each threshold level may correspond to a different impairment level. For example, the orientation threshold can include two different orientation threshold levels. A first orientation threshold level can correspond to a first impairment level and a second orientation threshold level can correspond to a second impairment level. When the sensor processor 410 determines that the orientation threshold exceeds the first orientation threshold level, the sensor processor 410 can adjust the signal parameters in accordance with the first impairment level. The sensor processor 410 can continue to monitor the foot orientation indicator and the foot acceleration, and to adjust the signal parameters based on any corresponding impairment levels.

The threshold levels may be predefined or may vary based on the operation of the FES system 102. The predefined threshold levels may be stored at the sensor unit 120. In some embodiments, the threshold levels may vary based on data previously collected by the sensor module 450. For example, the sensor processor 410 may lower an acceleration threshold if previously collected acceleration values are consistently low for an extended period of time. In that case, the sensor processor 410 can determine that the user 170 is navigating a relatively flat terrain and lower the acceleration threshold in order to adapt the FES system 102 to the relatively flat terrain by making the FES system 102 more sensitive to smaller changes in the terrain.

Each impairment level may, in some embodiments, correspond to a predefined set of signal parameters or predefined change to the signal parameters. For example, if the impairment level corresponds to a predefined set of signal parameters, the sensor processor 410 can define the signal parameters to correspond to predefined signal parameters associated with the corresponding impairment level. In some embodiments, if the impairment level corresponds to a predefined change to the signal parameters, the sensor processor 410 can define the signal parameters by increasing or decreasing the existing signal parameters by the predefined change.

In some embodiments, the sensor processor 410 may further adjust the signal parameters based on the environmental data. Temperature data collected by the sensor processor 410, for example, may be used for improving accuracy of data collected at the sensor module 450. For example, the sensor processor 410 may vary the stimulation signal based on temperature changes in the surrounding area of the user 170 since different weather conditions may affect the accuracy of data collected at the sensor module 450.

Once the sensor processor 410 adjusts the signal parameters, the sensor processor 410 and the communication module 430 can transfer the adjusted signal parameters to stimulation unit 110. The stimulation unit 110 can then generate the stimulation signal at least based on those signal parameters and apply the stimulation signal to the user 170 via the cuff 180 to adjust the orientation of the foot of the user 170.

Various embodiments of systems, device and methods that can be used to improve the gait of a user have been described here by way of example only. Various modifications and variations may be made to these example embodiments without departing from the spirit and scope of the embodiments, which is limited only by the appended claims. Also, in the various user interfaces illustrated in the figures, it will be understood that the illustrated user interface text and controls are provided as examples only and are not meant to be limiting. Other suitable user interface elements may be possible.

We claim:

1. A method of improving a gait of a user with a functional electrical stimulation (FES) orthotic system, the method comprising:
   receiving motion information associated with the gait of the user, the motion information comprising a foot acceleration and a foot angular velocity of the foot of the user;
   generating a foot orientation indicator for the foot based on the foot acceleration and the foot angular velocity, the foot orientation indicator corresponding to an angular position relative to a longitudinal axis of the foot, the foot orientation indicator comprising one or more orientation indicators each corresponding to a different direction of the angular position;
   determining a foot condition based on at least the foot orientation indicator and the foot acceleration, the foot condition indicating a gait quality of the user;
   determining the foot condition is a normal condition when the one or more orientation indicators is less than an orientation threshold and the foot acceleration is less than an acceleration threshold;
   determining the foot condition is an impaired condition when at least one of the orientation indicators is greater than or equal to the orientation threshold and the foot acceleration is greater than or equal to the acceleration threshold; and
   adjusting signal parameters for a stimulation signal based on at least the foot condition, the stimulation signal being applied to the user to adjust an orientation of the foot when the gait quality of the user requires improvement.

2. The method of claim 1, wherein the orientation threshold is approximately 15 degrees.

3. The method of claim 1, wherein the orientation threshold comprises a different orientation threshold for each of the different orientation indicators.

4. The method of claim 1, wherein the acceleration threshold is approximately 1.9 g.

5. The method of claim 1, wherein generating the foot orientation indicator for the foot further comprises compensating the foot angular velocity with the foot acceleration.

6. The method of claim 5, wherein the act of compensating comprises applying Kalman filtering to the foot acceleration and the foot angular velocity.

7. The method of claim 1, further comprising pre-processing each of the foot angular velocity and the foot acceleration to remove extraneous data.

8. The method of claim 7, wherein the step of pre-processing comprises applying a recurrence average filter for pre-processing.

9. The method of claim 1, wherein the method further comprises:
   receiving environmental data associated with a surrounding of the user; and
   adjusting the signal parameters for the stimulation signal based on the environmental data.

10. The method of claim 9, wherein the environmental data comprises a temperature of the surrounding environment of the user.

11. The method of claim 1, wherein the foot acceleration is received from an accelerometer.

12. The method of claim 1, wherein the foot angular velocity is received from a gyroscope.

13. The method of claim 1, wherein the motion information further comprises an amount of force exerted by the foot of the user that is used to determine if the user is taking a step or shifting their weight, wherein if the user is shifting their weight, the stimulation signal is not adjusted.

14. A functional electrical stimulation (FES) orthotic system for improving a gait of a user, the FES orthotic system comprising:
   a sensor unit comprising a sensor processor and a plurality of sensors, the sensor processor being configured to:
      receive motion information associated with the gait of the user, the motion information comprising a foot acceleration and a foot angular velocity of the foot of the user;
      receive environmental data associated with a surrounding of the user;

generate a foot orientation indicator for the foot based on the foot acceleration and the foot angular velocity, the foot orientation indicator corresponding to an angular position relative to a longitudinal axis of the foot;

determine a foot condition based on at least the foot orientation indicator and the foot acceleration, the foot condition indicating a gait quality of the user; and adjust signal parameters for a stimulation signal based on at least the foot condition and the environmental data, the stimulation signal being applied to the user to adjust an orientation of the foot when the gait quality of the user requires improvement.

15. The FES orthotic system of claim 14, wherein the foot orientation indicator comprises one or more orientation indicators and each of the one or more orientation indicators corresponds to a different direction of the angular position.

16. The FES orthotic system of claim 15, wherein the sensor processor is further configured to:

determine the foot condition is a normal condition when the orientation indicators is less than an orientation threshold and the foot acceleration is less than an acceleration threshold; and determine the foot condition is an impaired condition when at least one of the orientation indicators is greater than or equal to the orientation threshold and the foot acceleration is greater than or equal to the acceleration threshold.

17. The FES orthotic system of claim 16, wherein the orientation threshold is approximately 15 degrees.

18. The FES orthotic system of claim 16, wherein the orientation threshold comprises a different orientation threshold for each of the different orientation indicators.

19. The FES orthotic system of claim 15, wherein the acceleration threshold is approximately 1.9 g.

20. The FES orthotic system of claim 14, wherein the sensor processor is further configured to compensate the foot angular velocity with the foot acceleration.

21. The FES orthotic system of claim 20, wherein the sensor processor is further configured to apply a Kalman filter to the foot acceleration and the foot angular velocity.

22. The FES orthotic system of claim 14, wherein the sensor processor is further configured to pre-process each of the foot angular velocity and the foot acceleration to remove extraneous data.

23. The FES orthotic system of claim 22, wherein the sensor processor is further configured to apply a recurrence average filter for pre-processing.

24. The FES orthotic system of claim 14, wherein the environmental data comprises a temperature of the surrounding environment of the user.

25. The FES orthotic system of claim 14, wherein the sensor unit comprises an accelerometer to provide foot acceleration data.

26. The FES orthotic system of claim 14, wherein the sensor unit comprises a gyroscope to provide foot angular velocity data.

27. The FES orthotic system of claim 14, wherein the motion information further comprises an amount of force exerted by the foot that is used to determine if the user is taking a step or shifting their weight, wherein if the user is shifting their weight, the stimulation signal is not adjusted.

28. A non-transitory computer readable medium comprising a plurality of instructions executable on a processor of a device for adapting the processor to implement a method of improving a gait of a user with a functional electrical stimulation (FES) orthotic system, the computer readable medium comprising instructions for receiving motion information associated with the gait of the user, the motion information comprising a foot acceleration and a foot angular velocity of the foot of the user; generating a foot orientation indicator for the foot based on the foot acceleration and the foot angular velocity, the foot orientation indicator corresponding to an angular position relative to a longitudinal axis of the foot, the foot orientation indicator comprising one or more orientation indicators each corresponding to a different direction of the angular position; determining a foot condition based on at least the foot orientation indicator and the foot acceleration, the foot condition indicating a gait quality of the user; determining the foot condition is a normal condition when the one or more orientation indicators is less than an orientation threshold and the foot acceleration is less than an acceleration threshold; determining the foot condition is an impaired condition when at least one of the orientation indicators is greater than or equal to the orientation threshold and the foot acceleration is greater than or equal to the acceleration threshold; and adjusting signal parameters for a stimulation signal based on at least the foot condition, the stimulation signal being applied to the user to adjust an orientation of the foot when the gait quality of the user requires improvement.

* * * * *